(12) United States Patent
Daugan

(10) Patent No.: US 6,552,022 B1
(45) Date of Patent: Apr. 22, 2003

(54) BENZAMIDE DERIVATIVES AND THEIR USE AS APOB-100 SECRETION INHIBITORS

(75) Inventor: Alain Claude-Marie Daugan, Les Ulis (FR)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/831,844

(22) PCT Filed: Dec. 1, 1999

(86) PCT No.: PCT/EP99/09320

§ 371 (c)(1),
(2), (4) Date: May 15, 2001

(87) PCT Pub. No.: WO00/32582

PCT Pub. Date: Jun. 8, 2000

(30) Foreign Application Priority Data

Dec. 3, 1998 (GB) ................................ 9826412

(51) Int. Cl.$^7$ .................... A61K 31/495; A61K 31/496; C07D 295/155; C07D 401/06; C07D 403/06

(52) U.S. Cl. ............... 514/252.11; 514/253.01; 514/254.02; 514/254.03; 514/254.05; 514/254.1; 514/252.13; 514/254.09; 514/254.11; 514/255.03; 514/331; 544/357; 544/360; 544/367; 544/369; 544/370; 544/372; 544/373; 544/377; 544/379; 544/393; 546/230; 546/234

(58) Field of Search ................. 544/393, 357, 544/360, 367, 369, 370, 372, 373, 379, 377; 514/255.03, 252.11, 252.13, 253.01, 254.02, 254.03, 254.05, 254.1, 254.09, 254.11

(56) References Cited

U.S. PATENT DOCUMENTS 4,022,900 A   5/1977   Mathison
5,340,810 A * 8/1994   Clitherow et al.
5,356,893 A * 10/1994  Bradshaw et al.

FOREIGN PATENT DOCUMENTS

| EP | 0533267 A | 3/1993 |
| WO | WO96 40640 A | 12/1996 |
| WO | WO98 23593 A | 6/1998 |

OTHER PUBLICATIONS

"Advanced organic Chemistry" by Jerry Mar. (2nd Ed.), pp. 377–378 (1977).*

* cited by examiner

Primary Examiner—Emily Bernhardt
(74) Attorney, Agent, or Firm—Bonnie L. Deppenbrock

(57) ABSTRACT

The invention relates to therapeutic benzamide compounds of formula (I)

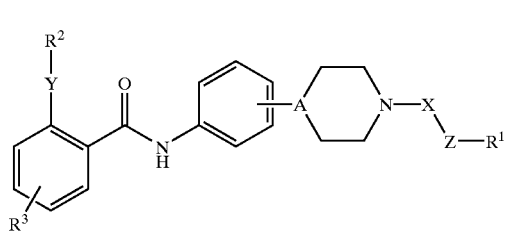

wherein A, X, Z, $R^1$, Y, $R^2$, $R^3$, are as defined herein, and physiologically acceptable salts, solvates or derivatives thereof. The present invention also provides pharmaceutical compositions, processes for the preparation of compounds of formula (I) and their use in the treatment of conditions mediated by ApoB-100 regulation.

12 Claims, No Drawings

BENZAMIDE DERIVATIVES AND THEIR USE AS APOB-100 SECRETION INHIBITORS

CROSS-REFERENCES TO RELATED APPLICATIONS

This application is a Rule 371 Application of PCT Application No. EP99/09320, filed Dec. 1, 1999, which claims priority to GB Application Serial No. 9826412.0, filed Dec. 3, 1998.

This invention relates to novel compounds which inhibit hepatic production of apoprotein B-100 (apoB-100), and to processes for their preparation, pharmaceutical compositions containing them and their medical use.

ApoB-100 is the main protein component of low density lipoprotein-cholesterol (LDL-C). High LDL-C plasmatic levels are a major risk factor for atherosclerosis and coronary, artery diseases. ApoB-100 plasmatic levels correlate with LDL-C plasmatic levels and also constitute a cardiovascular risk factor in themselves. ApoB-100 is exclusively produced by hepatocytes and reducing hepatic production of ApoB-100 should induce a decrease of LDL-C plasmatic levels.

Compounds having ApoB-100 inhibition properties have been described in WO96/40640, which is incorporated herein by reference.

DETAILED DESCRIPTION OF THE INVENTION

The present invention provides a compound of formula (I)

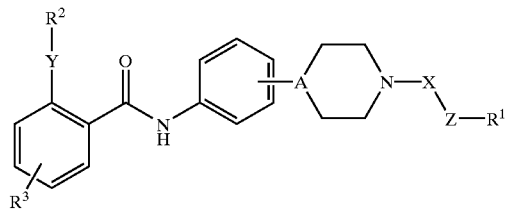

(I)

wherein

A represents N or CH;

X is selected from the following groups:
(i) —$C_{1-6}$alkylene-, optionally containing one or two double bonds and optionally substituted by one or more hydroxy, $C_{1-6}$alkyl, $C_{1-6}$alkoxy, $C_{1-6}$acyl or $C_{1-6}$acyloxy groups,
(ii) oxo, sulfonyl, thioxo,
(iii) —$C_{1-6}$alkylenecarbonyl-, —$C_{1-6}$alkylenesulfonyl-, —$C_{1-6}$alkylenethioxo-,
(iv) —$C_{2-6}$alkyleneoxy-, —$C_{2-6}$alkylenethio-, —$C_{2-6}$alkylene(N—H or N—$C_{1-6}$alkyl)amino-,
(v) —$C_{1-6}$alkylenecarboxy-, —$C_{1-6}$alkylenethioamido-, —$C_{1-6}$alkylene(N—H or N—$C_{1-6}$alkyl)carboxamido-, and
(vi) —$C_{2-6}$alkyleneoxycarbonyl-, —$C_{2-6}$alkylenethiocarbonyl-, —$C_{2-6}$alkylene(N—H or N—$C_{1-6}$alkyl)aminocarbonyl-;

Z represents a direct link or —$C_{1-6}$alkylene-, optionally containing one double bond and optionally substituted by one or more hydroxy, $C_{1-6}$alkyl, $C_{1-6}$alkoxy, $C_{1-6}$acyl or $C_{1-6}$acyloxy groups;

$R^1$ is selected from the following groups:
(i) hydrogen, $C_{1-3}$perfluoroalkyl,
(ii) $C_{6-10}$aryl, $C_{3-8}$cycloalkyl and fused benz derivatives thereof, $C_{7-10}$polycycloalkyl, $C_{4-8}$cycloalkenyl, $C_{7-10}$polycycloalkenyl,
(iii) a heterocyclyl selected from the group consisting of monocyclic radicals and fused polycyclic radicals, wherein said, radicals contain a total of from 5–14 ring atoms, wherein said radicals contain a total of from 1–4 ring heteroatoms independently selected from oxygen, nitrogen and sulfur, and wherein individual rings of said radicals may be independently saturated, partially unsaturated, or aromatic, and
(iv) where either X is $C_{1-6}$alkylene and Z is a direct link, or Z is $C_{1-6}$alkylene, $R^1$ additionally may represent a halogen, cyano, nitro or $C_{1-6}$acyl group, wherein, when $R^1$ contains one or more rings, said rings may each independently bear 0 to 4 substituents independently selected from
(i) halogen, hydroxy, cyano, nitro, formyl, $C_{1-6}$alkylsulfonylamino,
(ii) $C_{1-6}$alkyl, $C_{3-8}$cycloalkyl, $C_{1-3}$perfuoroalkyl,
(iii) $C_{1-6}$alkoxy, methylenedioxy, $C_{1-3}$perfuoroalkoxy, $C_{1-6}$alkylthio,
(iv) amino, $C_{1-6}$alkylamino, di-$C_{1-6}$alkylamino,
(v) phenyl, phenoxy, phenylthio, halophenylthio, benzyl, benzyloxy,
(vi) hydroxycarbonyl, $C_{1-6}$alkoxycarbonyl,
(vii) aminocarbonyl, $C_{1-6}$alkylaminocarbonyl, di-$C_{1-6}$alkylaminocarbonyl, di-$C_{1-6}$alkylaminocarbonyl$C_{1-6}$oxy, $C_{1-3}$perfluoroalkylaminocarbonyl,
(viii) $C_{1-6}$acyl, $C_{1-6}$acyloxy, $C_{1-6}$acyloxy$C_{1-6}$alkyl, $C_{1-6}$acylamino, and
(ix) an aromatic heterocyclyl consisting of monocyclic radicals, wherein said radicals contain 5–6 ring atoms, wherein said radicals contain a total of from 1–4 ring heteroatoms independently selected from oxygen, nitrogen and sulfur, and where each of the said heterocyclyl groups is optionally substituted by one or more groups independently selected from halogen, $C_{1-4}$alkyl, $C_{1-4}$alkoxy, $C_{1-3}$perfuoroalkyl and $C_{1-3}$perfuoroalkoxy;

Y represents a direct or oxy link, —$C_{1-6}$alkylene-, -oxy$C_{1-6}$alkylene- or a heterocyclyl consisting of monocyclic radicals, wherein said radicals contain 5 ring atoms, and wherein said radicals contain a total of from 1–4 ring heteroatoms independently selected from oxygen, nitrogen and sulfur and wherein the ring may be independently saturated, partially unsaturated, or aromatic;

$R^2$ represents phenyl, $C_{3-8}$cycloalkyl, or a heterocyclyl consisting of monocyclic radicals, wherein said radicals contain a total of from 5–6 ring atoms, wherein said radicals contain a total of from 1–4 ring heteroatoms independently selected from oxygen, nitrogen and sulfur, wherein the ring may be independently saturated, partially unsaturated, or aromatic, and where each $R^2$ is optionally substituted by one or more groups independently selected from halogen, $C_{1-4}$alkyl, $C_{1-4}$alkoxy, $C_{3-8}$cycloalkyl, $C_{1-3}$perfuoroalkyl, $C_{1-3}$perfuoroalkoxy, hydroxycarbonyl, $C_{1-6}$alkoxycarbonyl, cyano, nitro, $C_{1-4}$alkylaminosulfonyl;

$R^3$ represents hydrogen or one or more groups independently selected from halogen, $C_{1-4}$alkyl, $C_{1-4}$alkoxy, $C_{1-3}$ perfluoroalkyl or $C_{1-3}$ perfluoroalkoxy;

or a physiologically acceptable salt, solvate or derivative thereof.

Suitable physiologically acceptable salts of the compounds of general formula (I) include acid addition salts formed with pharmaceutically acceptable organic and inorganic acids for example, citrates, hydrochlorides, hydrobromides, or sulphates. Particularly preferred salts are citrates or hydrochloride salts.

The solvates may, for example, be hydrates.

References hereinafter to a compound according to the invention include both compounds of formula (I) and their physiologically acceptable salts together with physiologically acceptable solvates.

Referring to the general formula (I), alkyl, alkylene and alkoxy include both straight and branched chain saturated hydrocarbon groups. Examples of alkyl groups include methyl and ethyl groups, examples of alkylene groups include methylene and ethylene groups, whilst examples of alkoxy groups include methoxy and ethoxy groups.

Referring to general formula (I), a halogen atom may be a fluorine, chlorine, bromine or iodine atom.

Referring to the general formula (I), reference to heterocyclyl, unless otherwise defined, means any single ring or fused ring system containing at least one ring heteroatom independently selected from O, N and S. Thus, a polycyclic fused ring system containing one or more carbocyclic fused saturated, partially unsaturated, or aromatic rings (usually benz rings) is within the definition of heterocyclyl so long as the system also contains at least one fused ring which contains at least one of the aforementioned heteroatoms. As a substituent, such heterocyclyls may be attached to the remainder of the molecules from either a carbocyclic (e.g. benz) ring or from a heterocyclic ring.

Referring to the general formula (I), reference to $R^1$ as containing one or more rings is intended to mean any single or fused cyclic moiety or moieties attached to Z. The rings may be carbocyclic or heterocyclic, saturated or partially unsaturated, and aromatic or non-aromatic.

Reference to a polycyclic ring system or radical means that all rings in the system are fused.

Referring to the general formula (I), aryl means that the ring or substituent is carbocyclic and includes phenyl and naphthyl.

Referring to the general formula (I), acyl refers to aliphatic or cyclic hydrocarbons attached to a carbonyl group through which the substituent bonds.

Referring to the general formula (I), methylenedioxy refers to a x,x+1-methylenedioxy group, where x and x+1 are integers which represent the substitiution pattern on the ring, e.g. 3,4-methylenedioxy.

Referring to the general formula (I), $C_{1-3}$perfuoroalkyl or $C_{1-3}$perfuoroalkoxy includes compounds such as trifluoromethyl and trifluoromethoxy.

Suitably, the piperazine or piperidine group in formula (I) is substituted meta or para, most suitably para substituted. Preferably, A represents N.

X is suitably —$C_{1-6}$alkylene-, optionally containing by one double bond, e.g. methylene, ethylene, propylene or but-2-enylene, oxo, sulfonyl, —$C_{2-6}$alkyleneoxy-, e.g. ethyleneoxy or propyleneoxy, —$C_{1-6}$ alkylenecarboxy-, e.g. methylenecarboxy or —$C_{1-6}$alkylene(N—H or N—$C_{1-6}$alkyl)carboxamido-, e.g. methylene(N—H)carboxamido.

X is equally suitably methylene, oxo, or sulfonyl. As a preferred aspect, X is a methylene group.

Z is suitably a direct link or $C_{1-6}$alkylene, e.g. methylene or ethylene. Z is most suitably a direct link.

$R^1$ is suitably selected from the following groups
(i) hydrogen, cyano, $C_{1-3}$perfuoroalkyl, e.g. trifluoromethyl, (ii) optionally substituted phenyl, where optional substitution is effected by one or two groups independently selected from $C_{1-6}$ alkyl, e.g. methyl, cyano, halogen, e.g. fluoro, $C_{1-6}$alkoxy, e.g. methoxy, $C_{1-3}$perfuoroalkyl, e.g. trifluoromethyl, hydroxycarbonyl, $C_{1-4}$alkoxycarbonyl, e.g. methoxycarbonyl, aminocarbonyl, methylenedioxy, nitro, $C_{1-6}$ acyl, e.g. acetyl, phenyl, or an optionally substituted aromatic heterocycyl consisiting of monocyclic radicals and fused polycyclic radicals, wherein said radicals contain a total of 5 ring atoms, e.g. oxadiazolyl, where optional substitution is effected by $C_{1-4}$ alkyl, e.g. methyl, or $C_{1-3}$perfluoroalkyl, e.g. trifluoromethyl, or (iii) an optionally substituted aromatic heterocyclyl consisiting of monocyclic radicals and fused polycyclic radicals, wherein said radicals contain a total of from 5–10 ring atoms, e.g. indolyl, pyrrolyl, thienyl, furanyl, imidazolyl, pyrazolyl, thiazolyl, pyridyl or pyrazinyl, where optional substitution is effected by $C_{1-4}$alkyl, e.g. methyl, or halogen, e.g. fluorine.

Where $R^1$ is a substituted phenyl group, substitution is suitably in the 3-position.

When $R^1$ is an optionally substituted aromatic heterocyclyl, $R^1$ is preferably an optionally substituted pyrrolyl, where optional substitution is effected by a methyl group. Most preferably, the substitution pattern is 2-pyrrolyl.

$R^1$ is more suitably selected from the following groups
(i) hydrogen,
(ii) substituted phenyl, where substitution is effected by cyano or a methyl substituted oxadiazolyl group, or
(iii) a pyrrolyl group X—Z is suitably methylene or oxo and $R^1$ is suitably phenyl or a heterocyclyl, e.g. pyrrolyl, furanyl, C-linked imidazolyl, thienyl, pyrazolyl, thiazolyl, triazolyl, indolyl, pyridyl, N-Me-imidazolyl or pyrazinyl, where each $R^1$ is optionally substitued by one or more groups independently selected from $C_{1-6}$ alkyl, e.g. methyl, cyano, halogen, e.g. fluoro, $C_{1-6}$alkoxy, e.g. methoxy, trifluoromethyl, hydroxycarbonyl and $C_{1-4}$alkoxycarbonyl, e.g. methoxycarbonyl.

$R^1$ is preferably phenyl substituted by 3-cyano.

As a most preferred substitution pattern, —X—Z—$R^1$ is suitably aminocarbonylmethyl, pyrrolylmethyl or phenylmethyl substituted by cyano or methyl-oxadiazole.

Y is suitably a direct link, a 2,5-substituted oxazolyl group, or —$(CH_2)_n$—O—, where n is an integer from 0–3. More suitably, Y is a direct or oxy link. Preferably Y is a direct link.

$R^2$ is suitably cyclohexyl, a 5–6 membered aromatic heterocyclyl, e.g. pyrrolyl or pyridyl, or a phenyl group optionally substituted by one or two groups independently selected from halogen, e.g. fluoro or chloro, $C_{1-4}$ alkyl, e.g. methyl, ethyl or isopropyl, $C_{1-4}$ alkoxy, e.g. methoxy, or trifluoromethyl groups, where substitution is suitably in one or two of the 2-, 3-, or 4-positions on the phenyl ring. Preferably, $R^2$ is a phenyl group substituted by a trifluoromethyl group, most preferably in the 4-position. Equally preferably, $R^2$ is a phenyl group substituted by an isopropyl group, most preferably in the 4-position.

Preferably, Y is a direct link and $R^2$ is a phenyl group substituted by a trifluoromethyl or isopropyl group, most preferably in the 4-position.

$R^3$ is suitably hydrogen, halogen, e.g. chlorine, $C_{1-4}$ alkyl, e.g. methyl, $C_{1-3}$ perfluoroalkyl, e.g. trifluoromethyl or $C_{1-4}$ alkoxy e.g. methoxy. $R^3$ is more suitably hydrogen, halogen, e.g. chlorine, $C_{1-4}$ alkyl e.g. methyl or $C_{1-4}$ alkoxy e.g. methoxy. $R^3$ is preferably a hydrogen, methyl, methoxy or chloro group. R³ is equally preferably a hydrogen, methoxy or chloro group. Substitution is preferably in the 5 or 6 position.

Particularly preferred compounds of the invention include those in which each variable in Formula (I) is selected from the preferred groups for each variable. Even more preferable compoundsof the invention include those where each variable in Formula (I) is selected from the more preferred or most preferred groups for each variable.

A suitable sub-group of a compound of formula (I) is represented by formula (Ia)

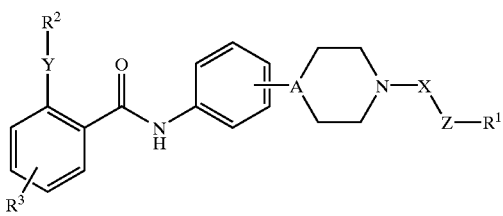

(Ia)

wherein

A is CH or N;

X is suitably $C_{1-6}$alkylene, optionally containing one double bond, oxo, sulfonyl, —$C_{2-6}$alkyleneoxy-, —$C_{1-6}$alkylenecarboxy- or —$C_{1-6}$alkylene(N—H or N—$C_{1-6}$alkyl)carboxamido;

Z represents a direct link or $C_{1-6}$alkylene;

R¹ represents one of the following groups
(i) hydrogen, $C_{1-3}$perfuoroalkyl,
(ii) optionally substituted phenyl, where optional substitution is effected by one or two groups independently selected from $C_{1-6}$ alkyl, cyano, halogen, $C_{1-6}$alkoxy, $C_{1-3}$perfuoroalkyl, hydroxycarbonyl, $C_{1-4}$alkoxycarbonyl, aminocarbonyl, $C_{1-3}$perfluoroalkylaminocarbonyl, methylenedioxy, nitro, $C_{1-6}$ acyl, phenyl, or an optionally substituted aromatic heterocyclyl consisting of monocyclic radicals and fused polycyclic radicals, wherein said radicals contain a total of 5 ring atoms, where optional substitution is effected by $C_{1-4}$alkyl, or $C_{1-3}$perfluoroalkyl,
(iii) an optionally substituted aromatic heterocycyl consisiting of monocyclic radicals and fused polycyclic radicals, wherein said radicals contain a total of from 5–10 ring atoms, where optional substitution is effected by $C_{1-4}$alkyl, or $C_{1-3}$perfluoroalkyl; or
(iv) where either X is $C_{1-6}$alkylene and Z is a direct link, or Z is $C_{1-6}$alkylene, R¹ additionally may represent a cyano group;

Y represents a direct or oxy link, a 5-membered aromatic heterocyclyl group, —$C_{1-6}$alkylene- or -oxy$C_{1-6}$alkylene-;

R² represents phenyl, $C_{3-8}$cycloalkyl, or an aromatic heterocycle containing 5–6 ring atoms and 1–4 ring heteroatoms, where each ring is optionally substituted by one or more groups independently selected from halogen, $C_{1-4}$alkyl, $C_{1-4}$alkoxy or $C_{1-3}$perfuoroalkyl;

R³ represents hydrogen, halogen, $C_{1-4}$alkyl or $C_{1-4}$alkoxy;

or a physiologically acceptable salt, solvate or derivative thereof.

A further suitable sub-group of a compound of formula (I) is represented by formula (Ib)

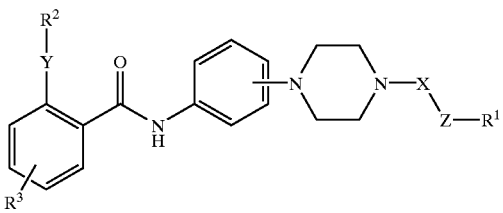

(Ib)

wherein

X is methylene, oxo or sulfonyl,

Z is selected from a direct link or NH, provided that if X is a methylene group, Z is a direct link;

R¹ is selected from the following groups:
(i) hydrogen
(ii) $C_{1-6}$alkoxy, $C_{1-6}$alkylthio,
(iii) $C_{1-6}$alkylamino, di-$C_{1-6}$alkylamino $C_{6-10}$ aryl$C_{1-6}$alkylamino, provided that Z is not NH,
(iv) unsubstuted vinyl, $C_{6-10}$aryl, $C_{3-8}$cycloalkyl, $C_{3-8}$cycoalkenyl,
(v) $C_{6-10}$ aryloxy
(vi) heterocyclyl selected from the group consisting of 5- and 6-membered heterocyclic radicals, which may be saturated, partially saturated, or aromatic, and the fused benz derivatives thereof, wherein said radicals may contain a total of from 1 to 3 ring heteroatoms independently selected from oxygen, nitrogen and sulfur, provided that if X is CH₂, R¹ is selected from groups (iv) and (vi)

wherein, when R¹ contains one or more rings, said rings may each independently bear 0 to 3 substituents independently selected from halogen, hydroxy, cyano, $C_{1-6}$alkyt, $C_{1-6}$alkoxy, $C_{1-6}$alkylaminocarbonyl, di-$C_{1-6}$alkylamino, di-$C_{1-6}$alkylaminocarbonyl, di-$C_{1-6}$alkylaminocarbonyl$C_{1-6}$alkoxy, $C_{1-6}$acyl, $C_{1-3}$perfuoroalkoxy, $C_{1-6}$acyloxy, hydroxycarbonyl and $C_{1-6}$alkoxycarbonyl;

Y represents a bond, an oxazolyl group, —O—, a —$C_{1-6}$alkylene- or an —O—$C_{1-6}$alkylene-group;

R² represents phenyl, $C_{3-8}$cycloalkyl, or a heterocycle containing 5–6 ring atoms and 1–4 ring heteroatoms, where each ring is optionally substituted by one or more groups independently selected from halogen, $C_{1-4}$alkyl, $C_{1-4}$alkoxy, $C_{3-8}$cycloalkyl, $C_{1-3}$perfuoroalkyl, $C_{1-3}$perfuoroalkoxy, $C_{1-6}$alkoxycarbonyl, cyano, phenyl, phenoxy, benzyl, benzyloxy;

R³ represents hydrogen or one or two groups independently selected from halogen, $C_{1-4}$alkyl or $C_{1-4}$alkoxy groups; or a physiologically acceptable salt, solvate or derivative thereof.

A yet further suitable sub-group of the invention is represented by a compound of formula (Ic)

(Ic)

wherein

X is methylene, oxo or sulfonyl, $R^1$ represents phenyl or a 5–6 membered aromatic heterocyclic group, said groups being optionally substitued by one or two groups independently selected from $C_{1-6}$ alkyl, cyano, halogen, $C_{1-6}$ alkoxy, trifluoromethyl, hydroxycarbonyl and $C_{1-6}$alkoxycarbonyl;

$R^2$ represents phenyl substituted by one or two groups independently selected from halogen, trifluoromethyl, $C_{1-4}$alkyl or $C_{1-4}$alkoxy groups;

$R^3$ represents hydrogen or one or two groups independently selected from halogen, $C_{1-4}$alkyl and $C_{1-4}$alkoxy groups;

or a physiologically acceptable salt, solvate or derivative thereof.

A yet further suitable sub-group of the invention is represented by a compound of formula (Id)

(Id)

wherein $R^1$ represents phenyl optionally substitued by one or two groups independently selected from $C_{1-6}$ alkyl, cyano, halogen, $C_{1-6}$ alkoxy, trifluoromethyl, hydroxycarbonyl and $C_{1-6}$alkoxycarbonyl;

$R^2$ represents phenyl substituted by one or two groups independently selected from halogen, trifluoromethyl, $C_{1-4}$alkyl and $C_{1-4}$alkoxy groups;

$R^3$ represents hydrogen or one or two groups independently selected from halogen, $C_{1-4}$alkyl and $C_{1-4}$alkoxy groups;

or a physiologically acceptable salt, solvate or derivative thereof.

A yet further suitable sub-group of the invention is represented.by a compound of formula (Ie)

(Ie)

wherein
  $R^1$ is selected from the following groups
    (i) aminocarbonyl,
    (ii) phenyl, optionally substituted by $C_{1-6}$alkyl, cyano, halogen, $C_{1-6}$alkoxy, $C_{1-3}$perfuoroalkyl, hydroxycarbonyl, $C_{1-4}$alkoxycarbonyl, aminocarbonyl, methylenedioxy, nitro, $C_{1-6}$acyl, phenyl, or an optionally substituted 5-membered aromatic heterocyclyl, where optional substitution is effected by $C_{1-4}$alkyl or $C_{1-3}$perfluoroalkyl, or
    (iii) an optionally substituted aromatic heterocycyl consisiting of monocyclic radicals and fused polycyclic radicals, wherein said radicals contain a total of from 5–10 ring atoms, where optional substitution is effected by $C_{1-4}$alkyl;
  $R^2$ represents phenyl, optionally substituted by one or two groups independently selected from halogen, $C_{1-3}$perfluoroalkyl, $C_{1-4}$alkyl and $C_{1-4}$alkoxy groups;
  $R^3$ represents hydrogen, halogen, $C_{1-4}$alkyl or $C_{1-4}$alkoxy;
or a physiologically acceptable salt, solvate or derivative thereof.

It will be clear that references herein to a compound of formula (I) apply equally to a compound of formula (Ia)–(Ie).

Particularly preferred compounds of the invention include those in which each variable of formula (I) is selected from the suitable groups for each variable. Even more preferable compounds of the invention include those where each variable in formula (I) is selected from the preferred or more preferred groups for each variable.

Suitable compounds according to the invention include:
  4'-Trifluoromethyl-biphenyl-2-carboxylic acid [4-[4-(3-cyano-benzyl)-piperazin-1-yl]-phenyl]-amide;
  4'-Isopropyl-5-methyl-biphenyl-2-carboxylic acid [4-[4-(3-cyano-benzyl)-piperazin-1-yl]-phenyl]-amide;
  4'-Isopropyl-6-methoxy-biphenyl-2-carboxylic acid [4-[4-(3-cyano-benzyl)-piperazin-1-yl]-phenyl]-amide;
  4'-Isopropyl-6-methyl-biphenyl-2-carboxylic acid [4-[4-(3-cyano-benzyl)-piperazin-1-yl]-phenyl]-amide;
  6-Methyl-4'-trifluoromethyl-biphenyl-2-carboxylic acid [4-[4-(3-cyano-benzyl)-piperazin-1-yl]-phenyl]-amide;
  4'-Isopropyl-5-methyl-biphenyl-2-carboxylic acid (4-{3-(3-methyl-[1,2,4]oxadiazol-5-yl)-benzyl]-piperazin-1-yl}-phenyl)-amide;
  5-Chloro-4'-isopropyl-biphenyl-2-carboxylic acid [4-[4-(3-cyano-benzyl)-piperazin-1-yl]-phenyl]-amide;
  6-Methoxy-4'-trifluoromethyl-biphenyl-2-carboxylic acid [4-[4-(3-cyano-benzyl)-piperazin-1-yl]-phenyl]-amide;
  5-Methyl-4'-trifluoromethyl-biphenyl-2-carboxylic acid [4-[4-(3-cyano-benzyl)-piperazin-1-yl]-phenyl]-amide;
  5-Chloro-4'-trifluoromethyl-biphenyl-2-carboxylic acid [4-[4-(3-cyano-benzyl)-piperazin-1-yl]-phenyl]-amide;
  Biphenyl-2-carboxylic acid (4-[4-(3-cyano-benzyl)-piperazin-1-yl]-phenyl]-amide;

5-Methoxy-biphenyl-2-carboxylic acid [4-[4-(3-cyano-benzyl)-piperazin-1-yl]-phenyl]-amide;
4-Chloro-4'-trifluoromethyl-biphenyl-2-carboxylic acid [4-[4-(3-cyano-benzyl)-piperazin-1-yl]-phenyt]-amide;
N-[4-[4-(3-Cyano-benzyl)-piperazin-1-yl]-phenyl]-2-phenoxy-benzamide;
N-[4-[4-(3-Cyano-benzyl)-piperazin-1-yl]-phenyl]-2-(5-phenyl-oxazol-2-yl)-benzamide;
4'-Isopropyl-biphenyl-2-carboxylic acid [4-[4-(3-cyano-benzyl)-piperazin-1-yl]-phenyl]-amide;
5-Methoxy-4'-trifluoromethyl-biphenyl-2-carbbxylic acid [4-[4-(3-cyano-benzyl)-piperazin-1-yl]-phenyl]-amide;
4-Methyl-4'-trifluoromethyl-biphenyl-2-carboxylic acid [4-[4-(3-cyano-benzyl)-piperazin-1-yl]-phenyl]-amide;
4-Methoxy-4'-trifluoromethyl-biphenyl-2-carboxylic acid [4-[4-(3-cyano-benzyl)-piperazin-1-yl]-phenyl]-amide;
4'-Ethyl-biphenyl-2-carboxylic acid [4-[4-(3-cyano-benzyl)-piperazin-1-yl]-phenyl]-amide;
4'-Methoxy-biphenyl-2-carboxylic acid [4-[4-(3-cyano-benzyl)-piperazin-1-yl]-phenyl]-amide;
3'-Trifluoromethyl-biphenyl-2-carboxylic acid [4-[4-(3-cyano-benzyl)-piperazin-1-yl]-phenyl]-amide;
4'-Fluoro-biphenyl-2-carboxylic acid [4-[4-(3-cyano-benzyl)-piperazin-1-yl]-phenyl]-amide;
3',4'-Dimethyl-biphenyl-2-carboxylic acid [4-[4-(3-cyano-benzyl)-piperazin-1-yl]-phenyl]-amide;
2',4'-Dimethyl-biphenyl-2-carboxylic acid [4-[4-(3-cyano-benzyl)-piperazin-1-yl]-phenyl]-amide;
3',4'-Dimethoxy-biphenyl-2-carboxylic acid [4-[4-(3-cyano-benzyl)-piperazin-1-yl]-phenyl]-amide;
N-[4-[4-(3-Cyano-benzyl)-piperazin-1-yl]-phenyl]-2-(4-trifluoromethyl-benzyloxy)-benzamide;
N-[4-[4-(3-Cyano-benzyl)-piperazin-1-yl]-phenyl]-3-methoxy-2-(4-trifluoromethyl-benzyloxy)-benzamide;
N-[4-[4-(3-Cyano-benzyl)-piperazin-1-yl]-phenyl]-2-(4-fluoro-benzyloxy)-3-methoxy-benzamide;
N-[4-[4-(3-Cyano-benzyl)-piperazin-1-yl]-phenyl]-3-methoxy-2-phenethyloxy-benzamide;
N-[4-[4-(3-Cyano-benzyl)-piperazin-1-yl]-phenyl]-2-(2-cyclohexyl-ethoxy)-3-methoxy-benzamide;
N-[4-[4-(3-Cyano-benzyl)-piperazin-1-yl]-phenyl]-2-(2-cyclohexyl-ethoxy)-benzamide;
N-[4-[4-(3-Cyano-benzyl)-piperazin-1-yl]-phenyl]-3-methoxy-2-(3-phenyl-propoxy)-benzamide
N-4-[4-(3-Cyano-benzyl)-piperazin-1-yl]-phenyl]-2-(4-fluoro-benzyloxy)-benzamide;
4'-Trifluoromethyl-biphenyl-2-carboxylic acid [3-[4-(3-cyano-benzyl)-piperazin-1-yl]-phenyl]-amide;
4'-Trifluoromethyl-biphenyl-2-carboxylic acid [4-(4-carbamoylmethyl-piperazin-1-yl)-phenyl]-amide;
4'-Isopropyl-6-methoxy-biphenyl-2-carboxylic acid [4-(4-carbamoylmethyl-piperazin-1-yl)-phenyl]-amide;
4'-Isopropyl-6-methyl-biphenyl-2-carboxylic acid [4-(4-carbamoylmethyl-piperazin-1-yl)-phenyl]-amide;
6-Methyl-4'-trifluoromethyl-biphenyl-2-carboxylic acid [4-(4-carbamoylmethyl-piperazin-1-yl)-phenyl]-amide
4'-Trifluoromethyl-biphenyl-2-carboxylic acid [4-(4-cyanomethyl-piperazin-1-yl)-phenyl]-amide;
4'-Trifluoromethyl-biphenyl-2-carboxylic acid [4-(4-ethoxycarbonylmethyl-piperazin-1-yl)-phenyl]-amide;
4'-Trifluoromethyl-biphenyl-2-carboxylic acid [4-(4-(2-ethoxy-ethyl)-piperazin-1-yl)-phenyl]-amide;
4'-Trifluoromethyl-biphenyl-2-carboxylic acid [4-(4-(3-hydroxy-propyl)-piperazin-1-yl]-phenyl]-amide;
4'-Trifluoromethyl-biphenyl-2-carboxylic acid [4-(4-(4,4,4-trifluoro-butyl)-piperazin-1-yl]-phenyl]-amide;
4'-Trifluoromethyl-biphenyl-2-carboxylic acid [4-(4-(3-methyl-but-2-enyl)-piperazin-1-yl]-phenyl]-amide;
4'-Trifluoromethyl-biphenyl-2-carboxylic acid [4-(4-(3-cyano-4-fluoro-benzyl)-piperazin-1-yl)-phenyl]-amide;
4'-Trifluoromethyl-biphenyl-2-carboxylic acid [4-(4-(3,4-methylenedioxy-benzyl)-piperazin-1-yl)-phenyl]-amide;
4'-Trifluoromethyl-biphenyl-2-carboxylic acid [4-(4-(3-nitro-benzyl)-piperazin-1-yl)-phenyl]-amide;
4'-Trifluoromethyl-biphenyl-2-carboxylic acid {4-[4-(3-carbamoyl-benzyl)-piperazin-1-yl]-phenyl}-amide;
4'-Trifluoromethyl-biphenyl-2-carboxylic acid [4-[4-(3-methoxy-benzyl)-piperazin-1-yl]-phenyl]-amide;
4'-Trifluoromethyl-biphenyl-2-carboxylic acid [4-[4-(4-fluoro-benzyl)-piperazin-1-yl]-phenyl]-amide;
4'-Trifluoromethyl-biphenyl-2-carboxylic acid [4-[4-(3-fluoro-benzyl)-piperazin-1-yl]-phenyl]-amide;
4'-Trifluoromethyl-biphenyl-2-carboxylic acid [4-(4-benzyl)-piperazin-1-yl]-phenyl]-amide;
4'-Trifluoromethyl-biphenyl-2-carboxylic acid [4-[4-(3-carbomethoxy-benzyl)-piperazin-1-yl]-phenyl]-amide;
4'-Trifluoromethyl-biphenyl-2-carboxylic acid [4-(4-pyridin-4-ylmethyl-piperazin-1-yl)-phenyl]-amide;
4'-Trifluoromethyl-biphenyl-2-carboxylic acid [4-(4-pyridin-2-ylmethyl-piperazin-1-yl)-phenyl]-amide;
4'-Trifluoromethyl-biphenyl-2-carboxylic acid [4-(4-pyrazin-2-ylmethyl-piperazin-1-yl)-phenyl]-amide;
4'-Trifluoromethyl-biphenyl-2-carboxylic acid [4-(4-thiazol-2-ylmethyl-piperazin-1-yl)-phenyl]-amide;
4'-Trifluoromethyl-biphenyl-2-carboxylic acid [4-[4-(1-methyl-1H-imidazol-2-ylmethyl)-piperazin-1-yl)-phenyl]-amide;
4'-Isopropyl-6-methyl-biphenyl-2-carboxylic acid (4-(4-(3-(3-methyl-[1,2,4]oxadiazol-5-yl)-benzyl)-piperazine-1-yl)-phenyl)-amide;
4'-Trifluoromethyl-biphenyl-2-carboxylic acid [4-(4-(1H-pyrrol-2-ylmethyl)-piperazin-1-yl)-phenyl]-amide;
4'-Isopropyl-5-methyl-biphenyl-2-carboxylic acid [4-(4-(1H-pyrrol-2-ylmethyl)-piperazin-1-yl)-phenyl]-amide;
5-Methyl-4'-trifluoromethyl-biphenyl-2-carboxylic acid [4-(4-(1H-pyrrol-2-ylmethyl)-piperazin-1-yl)-phenyl]-amide;
4'-Trifluoromethyl-biphenyl-2-carboxylic acid [4-(4-propyl-piperazin-1-yl)-phenyl]-amide;
4'-Trifluoromethyl-biphenyl-2-carboxylic acid [4-(4-(3-acetyl-benzyl)-piperazin-1-yl)-phenyl]-amide;
4'-Trifluoromethyl-biphenyl-2-carboxylic acid [4-(4-furan-2-ylmethyl-piperazin-1-yl)-phenyl]-amide;
4'-Isopropyl-6-methoxy-biphenyl-2-carboxylic acid [4-(4-(1H-pyrrol-2-ylmethyl)-piperazin-1-yl)-phenyl]-amide;
4'-Trifluoromethyl-biphenyl-2-carboxylic acid [4-(4-(1-methy)-1H-pyrrol-2-ylmethyl)-piperazin-1-yl)-phenyl]-amide;
4'-Trifluoromethyl-biphenyl-2-carboxytic acid [4-(4-thiophen-2-ylmethyl-piperazin-1-yl)-phenyl]-amide;

4'-Trifluoromethyl-biphenyl-2-carboxylic acid {4-[4-(1H-pyrazole-3-ylmethyl)-piperazine-1-yl]-phenyl}amide;

4'-Trifluoromethyl-biphenyl-2-carboxylic acid [4-(4-thiophen-3-ylmethyl-piperazin-1-yl)-phenyl]-amide;

4'-Trifluoromethyl-biphenyl-2-carboxylic acid {4-[4-(5-fluoro-1H-indol-3-ylmethyl)-piperazin-1-yl]-pheny}-amide;

4'-Isopropyl-6-methoxy-biphenyl-2-carboxylic acid (4-(4-(3-(3-methyl-[1,2,4]oxadiazol-5-yl)-benzyl)-piperazine-1-yl)-phenyl)-amide;

4'-Trifluoromethyl-biphenyl-2-carboxylic acid (4-{4-[3-(5-trifluoromethyl-[1,2,4]oxadiazol-3-yl)-benzyl]-piperazin-1-yl}-phenyl)-amide; (4-{4-[(4'-Trifluoromethyl-biphenyl-2-carbonyl)-amino]-phenyl}-piperazin-1-yl]-acetic acid;

4'-trifluoromethyl-biphenyl-2-carboxylic acid [4-(4-{[(biphenyl-3-ylmethyl)-carbamoyl]-methyl}-piperazin-1-yl)-phenyl]-amide;

3-(4-{4-[(4'-Trifluoromethyl-biphenyl-2-carbonyl)-amino]-phenyl}-piperazin-1 -ylmethyl)-benzoic acid;

4'-Trifluoromethyl-biphenyl-2-carboxylic acid (4-{4-[3-(2,2,2-trifluoro-ethylcarbamoyl)-benzyl]-piperazin-1-yl}-phenyl)-amide;

4'-Trifluoromethyl-biphenyl-2-carboxylic acid [4-[4-(3-cyano-benzoyl)-piperazin-1-yl]-phenyl]-amide;

4'-Trifluoromethyl-biphenyl-2-carboxylic acid [4-(4-acetyl-piperazin-1-yl)-phenyl]-amide;

4'-Trifluoromethyl-biphenyl-2-carboxylic acid [4-[4-(3-cyano-benzenesulfonyl)-piperazin-1-yl]-phenyl]-amide;

4'-Trifluoromethyl-biphenyl-2-carboxylic acid [4-(4-methanesulfonyl-piperazin-1-yl)-phenyl]-amide;

4'-Trifluoromethyl-biphenyl-2-carboxylic acid [4-[1-(3-cyano-benzyl)-piperidin-4-yl]-phenyl]-amide;

N-{4-[4-(3-Cyano-benzyl)-piperazin-1-yl]-phenyl}-2-pyrrol-1-yl-benzamide;

N-{4-[4-(3-Cyano-benzyl)-piperazin-1-yl]-phenyl}-2-pyridin-2-yl-benzamide;

or a physiologically acceptable salt, solvate or derivative thereof.

Preferred compounds of the invention include:

4'-Trifluoromethyl-biphenyl-2-carboxylic acid [4-[4-(3-cyano-benzyl)-piperazin-1 -yl]-phenyl]-amide;

4'-Isopropyl-5-methyl-biphenyl-2-carboxylic acid [4-[4-(3-cyano-benzyl)-piperazin-1-yl]-phenyl]-amide;

4'-Isopropyl-6-methoxy-biphenyl-2-carboxylic acid [4-[4-(3-cyano-benzyl)-piperazin-1-yl]-phenyl]-amide;

4'-Isopropyl-6-methyl-biphenyl-2-carboxylic acid [4-[4-(3-cyano-benzyl)-piperazin-1-yl]-phenyl]-amide;

6-Methyl-4'-trifluoromethyl-biphenyl-2-carboxylic acid [4-[4-(3-cyano-benzyl)-piperazin-1-yl]-phenyl]-amide;

4'-Isopropyl-5-methyl-biphenyl-2-carboxylic acid (4-{3-(3-methyl-[1,2,4]oxadiazol-5-yl)-benzyl]-piperazin-1-yl}-phenyl)-amide;

4'-Trifluoromethyl-biphenyl-2-carboxylic acid [4-(4-carbamoylmethyl-piperazin-1-yl)-phenyl]-amide;

4'-Isopropyl-6-methoxy-biphenyl-2-carboxylic acid [4-(4-carbamoylmethyl-piperazin-1-yl)-phenyl]-amide;

4'-Isopropyl-6-methyl-biphenyl-2-carboxylic acid [4-(4-carbamoylmethyl-piperazin-1-yl)-phenyl]-amide;

4'-Isopropyl-6-methyl-biphenyl-2-carboxylic acid (4-(4-(3-(3-methyl-[1,2,4]oxadiazol-5-yl)-benzyl)-piperazine-1-yl)-phenyl)-amide;

4'-Trifluoromethyl-biphenyl-2-carboxylic acid [4-(4-(1H-pyrrol-2-ylmethyl)-piperazin-1-yl)-phenyl]-amide;

4'-Isopropyl-5-methyl-biphenyl-2-carboxylic acid [4-(4-(1H-pyrrol-2-ylmethyl)-piperazin-1-yl)-phenyl]-amide;

5-Methyl-4'-trifluoromethyl-biphenyl-2-carboxylic acid [4-(4-(1H-pyrrol-2-ylmethyl)-piperazin-1-yl)-phenyl]-amide;

or a physiologically acceptable salt, solvate or derivative thereof.

The term "physiologically functional derivative" as used herein refers to any physiologically acceptable derivative of a compound of the present invention, for example, an ester, which upon administration to a mammal, such as a human, is capable of providing (directly or indirectly) such a compound or an active metabolite thereof. Such derivatives are clear to those skilled in the art, without undue experimentation, and with reference to the teaching of Burger's Medicinal Chemistry And Drug Discovery, 5th Edition, Vol 1: Principles And Practice, which is incorporated herein by reference.

The compounds of the invention are inhibitors of hepatic production of apoB-100 and are thus of use in the treatment of conditions resulting from elevated circulating levels of apoB-100.

The ability of the compounds of the invention to inhibit the production of apoB-100 by human hepatocytes in vitro is determined using primary human hepatocytes as a model system. The specificity of the compounds of the invention is established by comparing the effects on apoB-100, apoprotein A-1, and fibrinogen production. A specificity of at least 100 is preferred.

The in vivo profile of the compounds was determined by acute oral administration of the compounds of the invention to DBN/2 mice and Wistar rats with measurement of apoB-100 plasmatic levels as percentage of control values. Active compounds are further evaluated in Wistar rats by repeated oral administration (once a day) with measurement of total cholesterol, low density lipoprotein-cholesterol, triglycerides, apoB-100 and apoA-1 plasmatic levels as a percentage of control values.

The compounds of the invention are potent and specific inhibitors of hepatic production of apoB-100, which furthermore exhibit good oral bioavailability and duration of action.

Compounds of the invention are of use in the treatment of atherosclerosis, pancreatitis, non-insulin dependent diabetes mellitus (NIDDM), and coronary heart diseases.

Compounds of the invention are also useful in lowering serum lipid levels, cholesterol and/or triglycerides, and are of use in the treatment of hyperlipemia, hyperlipidemia, hyperlipoproteinemia, hypercholesterolemia and/or hypertriglyceridemia.

The invention therefore provides a compound of formula (I) or a physiologically acceptable salt, solvate or derivative thereof for use in therapy, in particular in human medicine.

There is also provided as a further aspect of the invention the use of a compound of formula (I) or a physiologically acceptable salt, solvate or derivative thereof in the preparation of a medicament for use in the treatment of conditions resulting from elevated circulating levels of apoB-100.

In an alternative or further aspect there is provided a method for the treatment of a mammal, including man, in particular in the treatment of conditions resulting from elevated circulating levels of apoB-100, comprising administration of an effective amount of a compound of formula (I) or a physiologically acceptable salt, solvate or derivative thereof.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one compound of formula (I) or a physiologically acceptable salt, solvate or derivative thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (i) may be formulated for oral, buccal, parenteral, transdermal, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifyIng agents (e.g. lecithin or acacia); non-aqueous vehicles (e.g. almond oil, oily esters, ethyl alcohol or fractionated vegetable oils); and preservatives (e.g. methyl or propyl p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

For transdermal administration the compounds according to the invention may be formulated as creams, gels, ointments or lotions or as a transdermal patch. Such compositions may for example be formulated with an aqueous or oily base with the addition of suitable thickening, gelling, emulsifyIng, stabilising, dispersing, suspending, and/or colouring agents.

The compounds of the invention may be formulated for parenteral administration by bolus injection or continuous infusion. Formulations for injection may be presented in unit dosageform e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions, may be formulated with an aqueous or oily base and will in general also contain one or more emulsifyIng agents, stabilising agents, dispersing agents, suspending agents, thickening agents, or colouring agents. Drops may be formulated with an aqueous or non aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unit dose device or alternatively as a powder mix with a suitable carrier for administration using a suitable delivery device.

The compositions may contain from 0.1% upwards, e.g. 0.1–99% of the active material, depending on the method of administration. A proposed dose of the compounds of the invention is 0.25 mg/kg to about 125 mg/kg bodyweight per day e.g. 20 mg/kg to 100 mg/kg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

The compounds of formula (I) may, if desired, be administered with one or more therapeutic agents and formulated for administration by any convenient route in a conventional manner. Appropriate doses will be readily appreciated by those skilled in the art. For example, the compounds of formula (I) may be administered in combination with an HMG CoA reductase inhibitor.

A compound of formula (I), or a physiologically acceptable salt, solvate or derivative thereof, may be prepared by the general methods outlined hereafter. In the following description, the groups X, Y, Z, $R^1$, $R^2$ and $R^3$ are as previously defined for compounds of formula (I), unless specified otherwise.

According to a general process (A), a compound of formula (I) may be prepared by reacting a compound of formula (II) with a compound of formula R'—Z—X—L

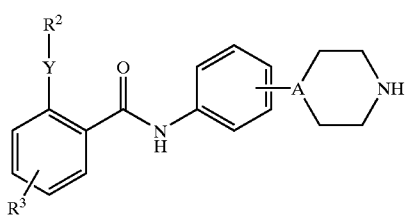

(II)

where L represents a suitable halide leaving group, e.g. chloride, under standard displacement conditions, or where X is an oxo group, L may additonally represent a hydroxy group, the reaction being effected under standard acid and amine coupling conditions.

A compound of formula (II) may be prepared by reaction of a compound of formula (III) with a compound of formula (IV)

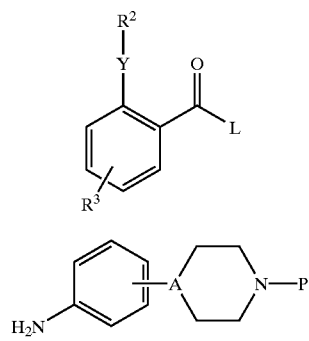

(III)

(IV)

where L is defined above and P is a suitable amine protecting group, e.g. tert-butoxycarbonyl (Boc), under standard coupling conditions for an acid and amine coupling, followed by deprotection of the protecting group under suitable conditions, e.g. acidic removal of a Boc group.

A compound of formula (IV), where A represents N, may be prepared by the two step reaction of a compound of formula (V)

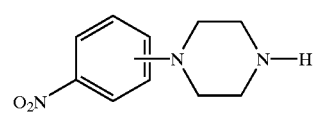

(V)

comprising incorporation of the protecting group P using standard methodology followed by reduction of the nitro group, e.g. under hydrogenation conditions.

A compound of formula (IV), where A represents CH, may be prepared from a compound of formula (VI)

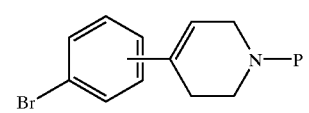

(VI)

by reaction with a suitable a compound of formula $H_2N-P'$ where P' is a suitable protecting group which is labile under hydrogenation conditions, such as a benzyl group, using a suitable coupling agent or agents such as tris(dibenzylidene acetone)dipalladium, 2,2'-bis(diphenylphosphino)-1,1'-binaphthyl (binap) and sodium tert-butoxide in a suitable solvent such as toluene, followed by removal of the protecting group and reduction of the double bond under hydrogenation conditions.

According to a second method (B), compounds of formula (I) may be prepared by reaction of compounds of formula (III) and compounds of formula (VII)

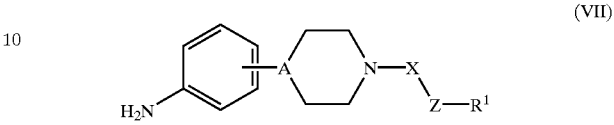

(VII)

where L is defined above, under standard coupling conditions.

Compounds of formula (VII) may be prepared by reaction of a compound of formula (V) With a compound of formula $R^1-Z-X-L$, where L is defined above, followed by reduction of the nitro group under hydrogenation or reductive tin chloride conditions.

According to a third process (C), a compound of formula (I) where Y is $-O-C_{1-4}$alkylene- may be prepared by reaction of a compound of formula (VIII) with a compound of formula $R^2-C_{1-4}$alkylene-L, where L is defined above,

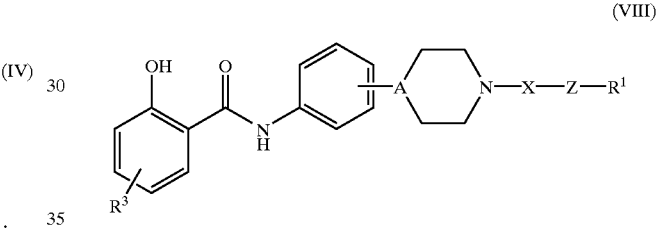

(VIII)

Compounds of formula (VIII) may be prepared according to the process outlined in process B.

According to a fourth general process (D), a compound of formula (I), where at least part of X represents an alkylene link to the piperidine or piperazine-group, may be prepared by reacting a compound of formula (II) with a compound of formula (IX)

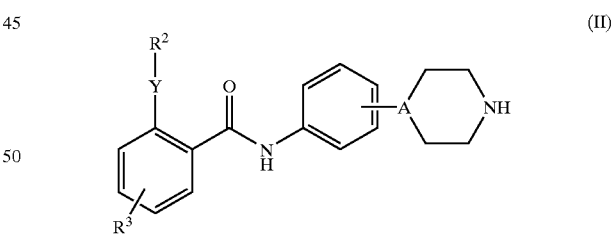

(II)

(IX)

where X' represents X minus a methylene group, under standard reductive amination conditions, e.g. using sodium triacetoxyborohydride in a solvent such as dichloroethane.

According to a fifth process (E), a compound of formula (I) may be prepared from a different compound of formula (I), using standard techniques well known in the art. For example, compounds of formula (I) where $R^1$ comprises a group containing an amide group may be prepared from the compound of formula (I) where the corresponding position comprises a carboxylic acid group, which in turn may be prepared from the compound of formula (I) where the corresponding position comprises a carboxylic ester group. Well known methods in the art may be employed to facilitate the transformation of an ester to an acid and then to an amide.

A compound of formula (III), where Y is a direct link, $R^2$ is a phenyl or an aromatic heterocyclyl and L is a hydroxy group, may be prepared firstly by coupling a boronic acid with a suitable leaving group, represented by a compound of formula (X) and a compound of formula (XI)

$R^{2'}$—A  (X)

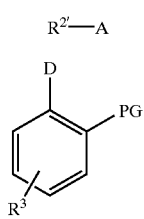

(XI)

where $R^{2'}$ represents phenyl or an aromatic heterocyclyl, PG represents a protected carboxylic acid and A and D represent either the boronic acid or the suitable leaving group, such as triflate or bromide, followed by deprotection of the protecting group under standard conditions, such as base removal of an ester group. Where L represents a halide leaving group, the carboxylic acid product can be treated with a suitable reagent, such as thionyl chloride, to give the corresponding chloride leaving group.

Where $R^1$ is a phenyl, substituted by an aromatic heterocyclyl, the aromatic heterocyclyl may be introduced by any well known methods in the art. For instance, where the substituent is a methyl substituted oxadiazole, this may be formed by treatment of a suitable benzamide derivative with a suitable reagent, such as dimethylacetamide dimethylacetal at elevated temperature, followed by cyclisation of the intermediate compound with hydoxylamine.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

Compounds of formula $R^1$—Z—X—L, (III), (V) and (VI), (IX), (X) and (XI) are known or may be prepared by standard methods well known in the art and/or herein described.

Physiologically acceptable salts may also be prepared from other salts, including other physiologically acceptable salts, of the compound of formula (I) using conventional methods.

The compounds of formula (I) may readily be isolated in association with solvent molecules by crystallisatioq from or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods.

Thus, in one example an appropriate optically active acid may be used to form salts with the enantiomeric mixture of a compound of general formula (I). The resulting mixture of isomeric salts may be separated, for example, by fractional crystallisation into the diastereoisomeric salts from which the required enantiomer of a compound of general formula (I) may be isolated by conversion into the required free base.

Alternatively, enantiomers of a compound of general forrmula (I) may be synthesised from the appropriate optically active intermediates using any of the general processes described herein.

The invention is further illustrated by the following intermediates and examples. All temperatures are in degrees centigrade.

Abbreviations:

MS-LCMS mass spectrography, HOBt-1-Hydroxybenzotriazole, AcOEt-Ethyl acetate, EDCl-1-(3-dimethylaminopropyl)-3-ethylcarbodiimide hydrochloride, BINAP-2,2'-bis(diphenylphosphino)-1,1'-binaphthyl, THF-Tetrahydrofuran, MeOH-Methanol, EtOH-Ethanol, $Et_3N$-Triethylamine

INTERMEDIATE 1

5-Methoxy-4'-trifluoromethyl-biphenyl-2-carboxylic Acid Methyl Ester

To a stirred solution of 4-methoxy-2-(trifluoro-methanesulfonyloxy)-benzoic acid methyl ester (6.28 g) in toluene (100 mL) was added LiCl (2.54 g) and $Pd(PPh_3)_4$ (1.15 g). After few minutes at room temperature, a 2M solution of $Na_2CO_3$ (26 mL) was added followed by a solution of 4-trifluoromethylphenyl boronic acid (4.17 g) in EtOH (30 mL). The resulting mixture was stirred under reflux for 6 hours. The mixture was cooled to room temperature and the phases were separated. The organic layer was then dried over $Na_2SO_4$, filtered and evaporated under reduced pressure. The residue was purified by flash chromatography eluting with hexane/AcOEt (90/10) to give the title compound (5.7 g) as white crystals.

m.p.: 93–94° C.

Simlilarly prepared were:

INTERMEDIATE 2

4'-Isopropyl-5-methyl-biphenyl-2-carboxylic acid methyl ester as an oil (10 g), GCMS: m/z 268 (M+) from 4-methyl-2-(trifluoro-methanesulfonyloxy)-benzoic acid methyl ester (11.9 g) and 4-isopropylphenyl boronic acid (7.2 g).

INTERMEDIATE 3

5-Methyl-4'-trifluoromethyl-biphenyl-2-carboxylic acid methyl ester as a pale yellow oil (4.2 g), GCMS: m/z 294(M+) from 4-methyl-2-(trifluoro-methanesulfonyloxy)-benzoic acid methyl ester (4.7 g) and 4-trifluoromethylphenyl boronic acid (3.3 g).

INTERMEDIATE 4

6-Methoxy-4'-trifluoromethyl-biphenyl-2-carboxylic acid methyl ester as an oil (6.8 g), GCMS: m/z 310 (M+) from 3-methoxy-2-(trifluoro-methanesulfonyloxy)-benzoic acid methyl ester (8.6 g) and 4-trifluoromethylphenyl boronic acid (5 g).

INTERMEDIATE 5

4'-Isopropyl-6-methoxy-biphenyl-2-carboxylic acid methyl ester as an oil (10 g), GCMS: m/z 284 (M+) from 3-methoxy-2-(trifluoro-methanesulfonyloxy)-benzoic acid methyl ester (12.2 g) and 4-isopropylphenyl boronic acid (7 g).

INTERMEDIATE 6

4'-Isopropyl-6-methyl-biphenyl-2-carboxylic acid methyl ester as a colorless oil (15.3 g), GCMS: m/z 268 (M+) from 3-methyl-2-(trifluoro-methanesulfonyloxy)-benzoic acid methyl ester (15.7 g) and 4-isopropylphenyl boronic acid (10 g).

INTERMEDIATE 7

6-Methyl-4'-trifluoromethyl-biphenyl-2-carboxylic acid methyl ester as a colorless oil (13.7 g), GCMS: m/z 294 (M+) from 3-methyl-2-(trifluoro-methanesulfonyloxy)-benzoic acid methyl ester (15.7 g) and 4-tnifluoromethylphenyl boronic acid (10 g).

INTERMEDIATE 8

2-(4'-Isopropyl-5-methoxy-biphenyl-2-yl)-4,4-dimethyl-4,5-dihydro-oxazole

To a suspension of magnesium (0.69 g) in $Et_2O$ (5 mL) containing a trace of iodine was added dropwise a solution of 1-bromo4-isopropyl-benzene (5.97 g) in $Et_2O$ (50 mL). Following the addition, the mixture was heated under reflux for 1 hour. The resulting grignard solution was then car-refully added to a solution of 2-(2,4-dimethoxy-phenyl)-4,4-dimethyl-4,5-dihydro-oxazole (3.52 g) in THF (60 mL) and the mixture was stirred at room temperature for 16 hours. The reaction mixture was then poured into saturated aqueous solution of $NH_4Cl$ and the mixture was extracted with $Et_2O$, dried over $Na_2SO_4$, filtered and evaporated under reduced pressure. The residue was purified by flash chromatography eluting with $CH_2Cl_2$/AcOEt (85/15) to give the title compound (3.5 g) as a pale yellow oil.

MS: m/z 324 (M+1).
Similarly prepared was:

INTERMEDIATE 9

2-(5-Chloro-4'-isopropyl-biphenyl-2-yl)-4,4-dimethyl-4,5-dihydro-oxazole as a yellow oil (7.5 g), MS: m/z 326 (M−1) from 2-(4-chloro-2-methoxy-phenyl)-4,4imethyl-4,5-dihydro-oxazole (10.2 g) and 1-bromo4-isopropyl-benzene (17.3 g).

INTERMEDIATE 10

5'-Chloro-2'-methyl-4-trifluoromethyl-biphenyl

To a solution of 2-bromo-4-chloro-toluene (20.5 g) in toluene (100 mL) was added $Pd(PPh_3)_4$ (1 g) and the mixture was stirred at room temperature under $N_2$ for 0.25 hours. A 2M solution of $Na_2CO_3$ (100 mL) was then added, followed by the dropwise addition of 4-trifluoromethylphenyl boronic acid (19 g) in MeOH (100 mL). The resulting mixture was heated under reflux for 48 hours. The mixture was then cooled to room temperature and the phases were separated. The organic layer was then dried over $Na_2SO_4$, filtered and evaporated under reduced pressure. The residue was purified by flash chromatography eluting with petroleum ether/AcOEt (90/10) to give the title compound (25.3 g) as a colorless liquid.

GCMS: m/z 270 (M+).

INTERMEDIATE 11

5-Methoxy-4'-trifluoromethyl-biphenyl-2-carboxylic Acid

5-Methoxy-4'-trifluoromethyl-biphenyl-2-carboxylic acid methyl ester (5.6 g) was placed in suspension in EtOH (80 mL) and a solution of NaOH (2.9 g) in water (40 mL) was added. The mixture was stirred under reflux for 2 hours and EtOH was evaporated under reduced pressure. The aqueous layer was then acidified with concentrated HCl and the resulting solid which formed was filtered, washed with water and dried to give the title compound (5.1 g) as white crystals. m.p.: 232–234° C.
Similarly prepared were:

INTERMEDIATE 12

4'-Isopropyl-5-methyl-biphenyl-2-carboxylic acid as white crystals (9 g), m.p.: 109–111° C. from 4'-isopropyl-5-methyl-biphenyl-2-carboxylic acid methyl ester (10 g).

INTERMEDIATE 13

5-Methyl-4'-trifluoromethyl-biphenyl-2-carboxylic acid as white crystals (3.7 g), m.p.: 176–178° C. from 5-methyl-4'-trifluoromethyl-biphenyl-2-carboxylic acid methyl ester (4.2 g).

INTERMEDIATE 14

6-Methoxy-4'-trifluoromethyl-biphenyl-2-carboxylic acid as white crystals (2.5 g), m.p.: 207–209° C. from 6-methoxy-4'-trifluoromethyl-biphenyl-2-carboxylic acid methyl ester (6.8 g).

INTERMEDIATE 15

4'-Isopropyl-6-methoxy-biphenyl-2-carboxylic acid as white crystals (8.4 g), m.p.: 132–134° C. from 4'-isopropyl-6-methoxy-biphenyl-2-carboxylic acid methyl ester (10 g).

INTERMEDIATE 16

4'-Isopropyl-6-methyl-biphenyl-2-carboxylc acid as white crystals (10 g), m.p.: 145–146° C. from 4'-isopropyl-6-methyl-biphenyl-2-carboxylic acid methyl ester (15.3 g).

INTERMEDIATE 17

6-Methyl-4'-trifluoromethyl-biphenyl-2-carboxylic acid as white crystals (8.5 g), m.p.: 206–208° C. from 6-methyl-4'-trifluoromethyl-biphenyl-2-carboxylic acid methyl ester (10 g).

INTERMEDIATE 18

4'-Isopropyl-5-methoxy-biphenyl-2-carboxylic Acid

A solution of 2-(4'-isopropyl-5-methoxy-biphenyl-2-yl)-4,4-dimethyl-4,5-dihydro-oxazole (3.4 g) in 4.5N HCl (200 mL) was stirred under reflux for 48 hours. The mixture was then cooled to room temperature and was extracted with $Et_2O$. The organic phase was then washed with brine, dried over $Na_2SO_4$, filtered and evaporated under reduced pressure to give the title compound (2.5 g) as an off white solid.
m.p.: 188–190° C.
Similarly prepared was:

INTERMEDIATE 19

5-Chloro-4'-isbpropyl-biphenyl-2-carboxylic acid as white crystals (2.2 g), m.p.: 145–147° C. from 2-(5-chloro-4'-isopropyl-biphenyl-2-yl)-4,4-dimethyl-4,5-dihydro-oxazole (7.5 g).

INTERMEDIATE 20

5-Chloro-4'-trifluoromethyl-biphenyl-2-carboxylic Acid

To a solution of 5'-chloro-2'-methyl-4-trifluoromethyl-biphenyl (27 g) in a mixture of t-butanol (100 mL) and $H_2O$ (200 mL) was added portionwise $KMnO_4$ (46.9 g). At the end of the addition, the mixture was heated under reflux for 16 hours, cooled to room temperature and filtered on celite. The filtrate was then acidified with concentrated HCl and the aqueous layer was extracted with AcOEt. The combined organic extracts were washed with brine, dried over $Na_2SO_4$, filtered and evaporated under reduced pressure to give the title compound (24 g) as white crystals.
m.p.: 174–176° C.

INTERMEDIATE 21
1-(3-Cyano-benzyl)-4-(4-nitro-phenyl)-piperazine

To a stirred solution of 1-(4-nitro-phenyl)-piperazine (35.9 g) and potassium carbonate (71.6 g) in acetone (500 mL) was added dropwise 3-cyano-benzyl bromide (34 g) at room temperature and the mixture was heated under reflux. After 4 hours, the salts were removed by filtration, washed with acetone and the filtrate was evaporated to dryness. The residue was taken in $CH_2Cl_2$ and the solution was washed with water, dried over $Na_2SO_4$, filtered and evaporated. The oily residue was crystallized from AcOEt/diisopropyl ether to give the title compound (52 g) as orange crystals.

m.p.: 120–122° C.

INTERMEDIATE 22
4-[4-(3-Cyano-benzyl)-piperazin-1-yl]-phenylamine

To a stirred solution of 1-(3-cyano-benzyl)-4-(4-nitro-phenyl)-piperazine (52 g) in EtOH (1.2 L) and THF (300 mL) was added portionwise $SnC_2.2H_2O$ (145.6 g) at room temperature and the mixture was heated at 55° C. for 16 hours. After evaporation of the solvents, the residue was taken in water, basified with NaOH at pH 14 and extracted with $CH_2Cl_2$. The organic layer was then washed with water, dried over $Na_2SO_4$, and evaporated. The residue was cristallized from disopropyl ether to give the title compound (40.5 g) as pale yellow crystals.

m.p.: 99–101° C.

INTERMEDIATE 23
N-[4-[3-Cyano-benzyl)-piperazin-1-yl]-phenyl]-2-hydroxy-benzamide To a stirred solution of 4-[4-(3-cyano-benzyl)-piperazin-1-yl]-phenylamine (2.24 g), 2-hydroxy-benzoic acid (1.08 g), HOBt (1.35 g), and Et3N (1 g) in $CH_2Cl_2$ (70 mL) was added at room temperature EDCl (1.9 g) and the mixture was stirred at room temperature for 4 hours. The organic solution was then washed with water, with a saturated solution of $NaHCO_3$, with brine and dried over $Na_2SO_4$. After filtration and evaporation of the filtrate, the residue was purified by flash chromatography eluting with $CH_2Cl_2$/MeOH (98/2) to[]give the title compound (1.85 g) as a yellow solid.

m.p.: 79–81° C.

Similarly prepared was:

INTERMEDIATE 24

N-[4-[3-Cyano-benzyl)-piperazin-1-yl]-phenyl]-2-hydroxy-3-methoxy-benzamide as pale yellow crystals (3.4 g), m.p.: 160–162° C. from 4-[4-(3-cyano-benzyl)-piperazin-1-yl]-phenylamine (4.39 g) and 2-hydroxy-3-methoxy-benzoic acid (2.56 g).

INTERMEDIATE 25
4-(4-Nitro-phenyl)-piperazine-1-carboxylic Acid tert-butyl Ester To a solution of 1-(4-nitro-phenyl)-piperazine (15.5 g) in $CH_2Cl_2$ (250 mL) was added $Et_3N$ (8.3 g). The solution was cooled to 0° C. and di-tert-butyl dicarbonate (17.1 g) was added portionwise. After 16 hours at room temperature, the solution was washed with water, with a saturated solution of $NaHCO_3$ and brine. The organic phase was dried over $Na_2SO_4$, filtered and evaporated under reduced pressure and the resulting solid was recrystallized from MeOH to give the title compound (21.5 g) as pale yellow crystals.

m.p.: 149–151° C.

INTERMEDIATE 26
4-(3-Nitro-phenyl)-piperazine-1-carboxylic Acid tert-butyl Ester To a solution of 1-iodo-3-nitro-benzene (9 g), piperazine-1-carboxylic acid tert-butyl ester (13.5 g) and sodium tert-butoxide (9.7 g) in dioxane (150 mL) was added tris(dibenzylideneacetone)dipalladium (2 g) and tri-o-tolylphosphine (2.2 g) and the mixture was heated at reflux for 24 hours. The solution was then cooled to room temperature, taken in $Et_2O$ and washed with brine. The organic layer was dried over $Na_2SO_4$, filtered and concentrated under reduced pressure. The crude residue was recrystallized from diisopropyl ether to give the title compound (6 g) as a yellow solid.

m.p.: 126–128° C.

INTERMEDIATE 27
4-(4-Amino-phenyl)-piperazine-1-carboxylic Acid tert-butyl Ester A solution of 4-(4-nitro-phenyt)-piperazine-1-carboxylic acid tert-butyl ester (21.4 g) in EtOH (250 mL) containing Pd/C 10% (0.5 g) was hydrogenated at room temperature. After 16 hours, the catalyst was removed by filtration and the filtrate was evaporated under reduced pressure. The oily residue was then crystallized from cyclohexane to give the title compound (17.8 g) as pink crystals.

m.p.: 95–96° C.

Similarly prepared was:

INTERMEDIATE 28

4-(3-Amino-phenyl)-piperazine-1-carboxylic acid tert-butyl ester as an oil (2.5 g), MS: m/z 278(M+1) from 4-(3-nitro-phenyl)-piperazine-1-carboxylic acid tert-butyl ester (6 g).

INTERMEDIATE 29
4-{4-[(4'-Trifluoromethyl-biphenyl-2-carbonyl)-amino]-phenyl}-piperazine-1-carboxylic Acid tert-butyl Ester Method A:

To a stirred solution of 4-(4-amino-phenyl)-piperazine-1-carboxylic acid tert-butyl ester (1.38 g), 4'-trifluoromethyl-biphenyl-2-carboxylic acid (1.33 g), HOBt (0.81 g), and $Et_3N$ (0.6 g) in $CH_2Cl_2$ (30 mL) was added EDCl (1.15 g) and the mixture was stirred at room temperature for 6 hours. The organic solution was then washed with water, with a saturated solution of $NaHCO_3$ and dried over $Na_2SO_4$. After filtration and evaporation of the filtrate, the residue was purified by flash chromatography eluting with $CH_2Cl_2$/AcOEt (90/10) and the resulting oily compound was crystallized from EtOH to give the title compound (2.3 g) as white crystals.

m.p.: 214–215° C.

Method B:

To a stirred solution of 4-(4-amino-phenyl)-piperazine-1-carboxylic acid tert-butyl ester (8.1 g) in $CH_2Cl_2$ (150 mL) was added $Et_3N$ (3.33 g) and the mixture was cooled at 0° C. To this solution was added dropwise 4'-trifluoromethyl-biphenyl-2-carbonyl chloride (8.53 g) in $CH_2Cl_2$ (80 mL) and the mixture was stirred at room temperature for 1 hour. The organic solution was then sequentially washed with water, with a saturated solution of $NaHCO_3$, with brine, then dried over $Na_2SO_4$, filtered and evaporated. The oily residue by trituration from diisopropyl ether give the title compound (13.6 g) as white crystals.

m.p.: 213–215° C.

INTERMEDIATE 30

4-{4-[(4'-Isopropyl-5-methyl-biphenyl-2-carbonyl)-amino]-phenyl}-piperazine-1-carboxylic Acid tert-butyl Ester To a stirred solution of 4-(4-amino-phenyl)-piperazine-1-carboxylic acid tert-butyl ester (4.15 g), 4'-isopropyl-5-methyl-biphenyl-2-carboxylic acid (3.81 g), HOBt (2.36 g), and Et$_3$N (1.97 g) in CH$_2$Cl$_2$ (50 mL) was added EDCl (3.72 g) and the mixture was stirred at room temperature for 16 hours. The organic solution was then washed with water, with a saturated solution of NaHCO$_3$, with brine and dried over Na$_2$SO$_4$. After filtration and evaporation of the filtrate, the residue was crystallized from diisopropyl ether to give the title compound (4 g) as white crystals.

m.p.: 173–175° C.

Similarly prepared were:

INTERMEDIATE 31

4-{4-[(4'-Isopropyl-6-methoxy-biphenyl-2-carbonyl)-amino]-phenyl}-piperazine-1-carboxylic acid tert-butyl ester as white crystals (1.9 g), m.p.:, 155–157° C. from 4'-isopropyl-6-methoxy-biphenyl-2-carboxylic acid (1.94 g) and 4-(4-amino-phenyl)-piperazine-1-carboxylic acid tert-butyl ester (2 g).

INTERMEDIATE 32

4-{4-[(6-Methyl-4'-trifluoromethyl-biphenyl-2-carbonyl)-amino]-phenyl}-piperazine-1-carboxylic acid tert-butyl ester as white crystals (1.5 g), m.p.: 163–165° C. from 6-methyl-4'-trifluoromethyl-biphenyl-2-carboxylic acid (2 g) and 4-(4-amino-phenyl)-piperazine-1-carboxylic acid tert-butyl ester (2 g).

INTERMEDIATE 33

4-{4-[(4'-Isopropyl-6-methyl-biphenyl-2-carbonyl)-amino]-phenyl}-piperazine-1-carboxylic acid tert-butyl ester as white crystals (1.8 g), m.p.: 140–142° C. from 4'-isopropyl-6-methyl-biphenyl-2-carboxylic acid (1.83 g) and 4-(4-amino-phenyl)-piperazine-1-carboxylic acid tert-butyl ester (2 g).

INTERMEDIATE 34

4-{4-[2-(4-Fluoro-benzyloxy)-benzoylamino]-phenyl}-piperazine-1-carboxylic acid tert-butyl ester as white crystals (6.7 g), m.p.: 170–171° C. from 4-(4-amino-phenyl)-piperazine-1-carboxylic acid tert-butyl ester (4.15 g) and 2-(4-fluoro-benzyloxy)-benzoic acid (3.69 g).

INTERMEDIATE 35

4-{3-[(4'-Trifluoromethyl-biphenyl-2-carbonyl)-amino]-phenyl}-piperazine-1-carboxylic acid tert-butyl ester as a white solid (3.3 g), m.p.: 160° C. from 4-(3-amino-phenyl)-piperazine-1-carboxylic acid tert-butyl ester (2.5 g) and 4'-tnfluoromethyl-biphenyl-2-carboxylic acid (2.5 g).

INTERMEDIATE 36

4'-Trifluoromethyl-biphenyl-2-carboxylic Acid (4-piperazin-1-yl-phenyl)-amide

To a solution of 4-{4-[(4'-trifluoromethyl-biphenyl-2-carbonyl)-amino)-phenyl}-piperazine-1-carboxylic acid tert-butyl ester (11.7 g) in CH$_2$Cl$_2$ (50 mL) was added trifluoroacetic acid (25 mL) and the solution was stirred at room temperature for 2 hours. The mixture was then evaporated under reduced pressure and the residue was taken in water. The resulting precipitate was filtered and washed with water. The resulting solid was then suspended in water, basified with a saturated solution of Na$_2$CO$_3$, and extracted with CH$_2$Cl$_2$. The organic phase was then washed with water, dried over Na$_2$SO$_4$, filtered and evaporated to give the title compound (9 g) as white crystals.

m.p.: 119–124° C.

INTERMEDIATE 37

4'-Isopropyl-5-methyl-biphenyl-2-carboxylic Acid (4-piperazin-1-yl-phenyl)-amide To a solution of 4-{4-[(4'-isopropyl-5-methyl-biphenyl-2-carbonyl)-amino]-phenyl}-piperazine-1-carboxylic acid tert-butyl ester (4 g) in CH$_2$Cl$_2$ (20 mL) was added trifluoroacetic acid (15 mL) and the solution was stirred at room temperature for 16 hours. The mixture was then evaporated under reduced pressure and the residue was taken in water and basified with a 1N NaOH aqueous solution. The resulting precipitate was extracted with CH$_2$Cl$_2$ and the organic phase was washed with water, dried over Na$_2$SO$_4$ filtered and evaporated to give the title compound (3 g) as white crystals.

m.p.: 131–133° C.

Similarly prepared were

INTERMEDIATE 38

4'-Isopropyl-6-methoxy-biphenyl-2-carboxylic acid (4-piperazin-1-yl-phenyl)-amide as white crystals (1.3 g), m.p.: 157–159° C. from 4-{4-[(4'-isopropyl-6-methoxy-biphenyl-2-carbonyl)-amino]-phenyl}-piperazine-1-carboxylic acid tert-butyl ester (1.9 g).

INTERMEDIATE 39

6-Methyl-4'-trifluoromethyl-biphenyl-2-carboxylic acid (4-piperazin-1-yl-phenyl)-amide as white crystals (0.9 g), m.p.: 155–157° C. from 4-{4-[(6-methyl-4'-trifluoromethyl-biphenyl-2-carbonyl)-amino]-phenyl}-piperazine-1-carboxylic acid tert-butyl ester (1.5 g).

INTERMEDIATE 40

4'-Isopropyl-6-methyl-biphenyl-2-carboxylic acid (4-piperazin-1-yl-phenyl)-amide as white crystals (1.2 g), m.p.: 130° C. from 4-{4-[(4'-isopropyl-6-methyl-biphenyl-2-carbonyl)-amino]-phenyl}-piperazine-1-carboxylic acid tert-butyl ester (1.8 g).

INTERMEDIATE 41

2-(4-Fluoro-benzyloxy)-N-(4-piperazin-1-yl-phenyl)-benzamide as white crystals (3.6 g), m.p.: 143–146° C. from 4-{4-[2-(4-fluoro-benzyloxy)-benzoylamino]-phenyl}-piperazine-1-carboxylic acid tert-butyl ester (6 g).

INTERMEDIATE 42

4'-Trifluoromethyl-biphenyl-2-carboxylic acid (3-piperazin-1-yl-phenyl)-amide as white crystals (2.5 g), m.p.: 101–103° C. from 4-{3-[(4'-trifluoromethyl-biphenyl-2-carbonyl)-amino]-phenyl}-piperazine-1-carboxylic acid tert-butyl ester (3.3 g).

INTERMEDIATE 43

4-(4-Bromo-phenyl)-3,6-dihydro-2H-pyridine-1-carboxylic Acid tert-butyl Ester

To a solution of 4-(4-bromo-phenyl)-1,2,3,6-tetrahydro-pyridine (2.39 g) in CH$_2$Cl$_2$ (30 mL) was added Et$_3$N (2 g). The solution was cooled at 0° C. and di-tert-butyl dicarbonate (2.29 g) was added. After 16 hours at room temperature, the solution was washed with water, with a saturated solu-

INTERMEDIATE 44
4-(4-Benzylamino-phenyl)-3,6-dihydro-2H-pyridine-1-carboxylic Acid tert-butyl Ester To a solution of 4-(4-bromo-phenyl)-3,6-dihydro-2H-pyridine-1-carboxylic acid tert-butyl ester (0.34 g), benzylamine (0.12 g) and sodium tert-butoxide (0.13 g) in toluene (8 mL) were added tris(dibenzylidene acetone)dipalladium (2.2 mg) and Binap (4.6 mg) and the mixture was heated at 80° C. for 16 hours. The solution was then cooled to room temperature, filtered and the filtrate was evaporated under reduced pressure. The residue was purified by flash chromatography eluting with petroleum ether/AcOEt (90/10) and the oily residue was crystallized from diisopropyl ether to give the title compound (0.27 g) as white crystals.

m.p.: 120–121° C.

INTERMEDIATE 45
4-(4-Aminophenyl)-piperidine-1-carboxylic Acid tert-butyl Ester A solution of 4-(4-benzylamino-phenyl)-3,6-dihydro-2H-pyridine-1-carboxylic acid tert-butyl ester (0.27 g) in EtOH (10 mL) containing Pd/C 10% (50 mg) was hydrogenated at room temperature. After 1 hour, the catalyst was removed by filtration and the filtrate was evaporated under reduced pressure to give the title compound (0.18 g) as a pale pink oil.

MS: m/z 277(M+1).

INTERMEDIATE 46
4-{4-[(4'-Trifluoromethyl-biphenyl-2-carbonyl)-amino]-phenyl}-piperidine-1-carboxylic Acid tert-butyl Ester To a stirred solution of 4-(4-aminophenyl)-piperidine-1-carboxylic acid tert-butyl ester (0.18 g), 4'-trifluoromethyl-biphenyl-2-carboxylic acid (0.17 g), HOBt (0.1 g), and Et$_3$N (80 mg) in CH$_2$Cl$_2$ (10 mL) was added at room temperature EDCl (0.15 g) and the mixture was stirred at room temperature for 16 hours. The organic solution was then washed with water, with a saturated solution of NaHCO$_3$ and dried over Na$_2$SO$_4$. After filtration and evaporation of the filtrate, the residue was purified by flash chromatography eluting with petroleum ether/AcOEt (70/30) to give the title compound (0.25 g) as an orange oil.

MS: m/z 523(M−1).

INTERMEDIATE 47
4'-Trifluoromethyl-biphenyl-2-carboxylic Acid (4-piperidin-4-yl-phenyl)-amide as Trifluoroacetate Salt To a solution of 4-{4-[(4'-trifluoromethyl-biphenyl-2-carbonyl)-amino]-phenyl}-piperidine-1-carboxylic acid tert-butyl ester (0.22 g) in CH$_2$Cl$_2$ (5 mL) was added trifluoroacetic acid (1 mL) and the solution was stirred at room temperature for 1 hour. The mixture was evaporated under reduced pressure and the residue taken in water. The resulting precipitate was filtered, washed with water and dried to give the title compound (0.23 g) as white crystals.

m.p.: 223–225° C.

INTERMEDIATE 48
3-[1,3]Dioxolan-2-yl-benzamide

To a solution of 3-(1,3-dioxolan-2-yl)-benzonitrile (5.86 g) in a mixture of EtOH (140 mL) and H$_2$O (60 mL) was added sodium hydroxide (6.46 g) and the mixture was heated under reflux for 2 hours. The solvent was evaporated under reduced pressure and the aqueous layer was extracted with CH$_2$Cl$_2$. The organic phase was washed with water, dried over Na$_2$SO$_4$, filtered and evaporated to give the title compound (4.5 g) as a white solid.

m.p.: 92–94° C.

INTERMEDIATE 49
3-(3-Methyl-[1,2,4]oxadiazol-5-yl)-benzaldehyde

A mixture of 3-[1,3]dioxolan-2-yl-benzamide (2.3 g) and dimethylacetamide dimethylacetal (4 g) was heated under reflux for 1 hour and then evaporated to dryness. The oily residue was dissolved in dioxane (20 mL) and hydroxylamine hydrochloride (1.18 g), acetic acid (20 mL) and a 2N aqueous sodium hydroxide solution (9 mL) were added and the mixture was heated at 90° C. for 2 hours. After evaporation, the residue was dissolved in toluene (100 mL) and a 1N hydrochloric acid solution (50 mL) was added and the mixture was stirred at reflux for 2 hours. After cooling at room temperature the organic phase was decanted, washed with water, dried over Na$_2$SO$_4$, filtered and evaporated to give the title compound (2.3 g) as a white solid.

m.p.: 114–116° C.

INTERMEDIATE 50
[4-(4-Benzyl-piperazine-1-yl)-phenyl]-carbamic Acid tert-butyl Ester To a solution of 4-(4-benzyl-piperazine-1-yl)-phenylamine (32 g) in CH$_2$Cl$_2$ (500 mL) containing Et$_3$N (18.4 mL) was added dropwise di-tert-butyl dicarbonate (28.8 g) at 0° C. After 20 hours at room temperature, the solution was washed with water, with a saturated solution of NaHCO$_3$ and brine. The organic phase was dried over Na$_2$SO$_4$, filtered and evaporated under reduced pressure to give the title compound (43.5 g) as a solid.

GCMS: m/z 367 (M+).

INTERMEDIATE 51
(4-Piperazin-1-yl-phenyl)-carbamic Acid tert-butyl Ester

A solution of [4-(4-benzyl-piperazine-1-yl)-phenyl]-carbamic acid tert-butyl ester (43.5 g) in EtOH (1 L) containing Pd/C 10% (4 g) was hydrogenated at room temperature. After 72 hours, the catalyst was removed by filtration and the filtrate was evaporated under reduced pressure. The oily residue was then purified by flash chromatography eluting with AcOEt/isopropylamine (90/10) and the solid obtained was recristallized from AcOEt to give the title compound (17.5 g) as white crystals.

m.p.: 155–157° C.

INTERMEDIATE 52
(4-{4-[3-(3-Methyl-[1,2,4]oxadiazo)-5-yl)-benzyl]-piperazin-1-yl}-phenyl)-carbamic Acid tert-butyl Ester To a solution of (4-piperazin-1-yl-phenyl)-carbamic acid tertbutyl ester (2 g) in 1,2-dichloroethane (80 mL) was added 3-(3-methyl-[1,2,4]oxadiazol-5-yl)-benzaldehyde (1.4 g) and acetic acid (0.67 g). The solution was cooled at 0° C. and sodium triacetoxy borohydride (3.15 g) was added portionwise and the mixture was stirred at room temperature for 16 hours. The solution was then washed with a saturated solution of NaHCO$_3$, with brine, dried over Na$_2$SO$_4$, filtered and evaporated under reduced pressure. The residue was purified by flash chromatography eluting with CH$_2$Cl$_2$/MeOH (98/2) to give the title compound (2.5 g) as a white solid.

m.p.: 159–161° C.

INTERMEDIATE 53
4-{4-[3-(3-Methyl-[1,2,4]oxadiazol-5-yl)-benzyl-1-piperazin-1-yl}-phenylamine To a stirred solution of (4-{4-[3-(3-methyl-[1,2,4]oxadiazol-5-yl)-benzyl]-piperazin-1-yl}-phenyl)-carbamic acid tert-butyl ester (2.5 g) in $CH_2Cl_2$ (4 mL) was added trifluoroacetic acid (6 mL) and the mixture was stirred at room temperature for 16 hours. After evaporation under reduced pressure, the residue was taken in water, basified with a 1N NaOH aqueous solution and extracted with $CH_2Cl_2$. The organic phase was then washed with water, dried over $Na_2SO_4$, filtered and evaporated. The oily residue was crystallized from $MeOH/H_2O$ to give the title compound (1.35 g) as a solid.

m.p.: 106–108° C.

INTERMEDIATE 54
3-(5-Trifluoromethyl-[1,2,4]oxadiazol-3-yl)-benzaldehyde

To a stirred solution of 3-(1,3-dioxolan-2-yl)-benzonitrile (4 g) in EtOH (130 mL) was added hydroxylamine hydrochloride (7.9 g) and potassium carbonate (15.7 g) and the mixture was refluxed for 4 hours. The hot mixture was filtered and the remaining solids were washed with EtOH and the filtrate was evaporated under reduced pressure. The crude amidoxime (4.2 g) was dissolved in trifluoroacetic acid (20 mL) and $Et_3N$ (2 g) was added and the mixture was stirred at room temperature for 3 hours. The solution was evaporated to dryness and the residue was extracted with $CH_2Cl_2$. The organic phase was washed with water, dried over $Na_2SO_4$, filtered and evaporated. The residue was then dissolved in toluene (100 mL) and 1N aqueous hydrochloric acid (30 mL) was added and the mixture was heated at reflux for 1 hour. The mixture was cooled to room temperature, the organic phase was decanted and washed with brine, dried over $Na_2SO_4$, filtered and evaporated. The residue was purified by flash chromatography eluting with $CH_2Cl_2$ to give the title compound (2 g) as a pale yellow oil.

GCMS: m/z 242 ($M^+$).

EXAMPLE 1
4'-Trifluoromethyl-biphenyl-2-carboxylic Acid [4-[4-(3-cyano-benzyl)-piperazin-1-yl]-phenyl]-amide (Method 1)

To a stirred solution of 4-[4-(3-cyano-benzyl)-piperazin-1-yl]-phenylamine (0.29 g), 4'-trifluoromethyl-biphenyl-2-carboxylic acid (0.26 g), HOBt (0.16 g), and $Et_3N$ (0.12 g) in $CH_2Cl_2$ (15 mL) was added at room temperature EDCl (0.23 g) and the mixture was stirred at room temperature for 4 hours. The organic solution was then washed with water, with a saturated solution of $NaHCO_3$ and dried over $Na_2SO_4$. After filtration and evaporation of the filtrate, the residue was purified by flash chromatography eluting with $CH_2Cl_2/AcOEt$ (90/10) and the solid obtained was recrystallized from EtOH to give the title compound (0.48 g) as white crystals.

m.p.: 149–150° C.

Analysis for $C32H27F3N4O$ Calculated: C,71.10; H,5.03; N,10.36; Found: $C_{,70.82}$; H,5.35; N,10.19%.

EXAMPLE 2
4'-Isopropyl-5-methyl-biphenyl-2-carboxylic Acid [4-[4-(3-cyano-benzyl)-piperazin-1-yl]-phenyl]-amide To a stirred solution of 4-[4-(3-cyano-benzyl)-piperazin-1-yl]-phenylamine (150 mg), 4'-isopropyl-5-methyl-biphenyl-2-carboxylic acid (127 mg), HOBt (87 mg), and $Et_3N$ (64 mg) in $CH_2Cl_2$ (10 mL) was added at room temperature EDCl (124 mg) and the mixture was stirred at room temperature for 16 hours. The organic solution was then washed with water, with a saturated solution of $NaHCO_3$ and dried over $Na_2SO_4$. After filtration and evaporation of the filtrate, the oily residue was crystallized from EtOH to give the title compound (160 mg) as white crystals.

m.p.: 167–169° C.

Analysis for $C35H36N4O$ Calculated: C,79.51; H,6.86; N,10.60; Found: C,79.41; H,6.61; N,10.81%.

EXAMPLE 3
4'-Isopropyl-6-methoxy-biphenyl-2-carboxylic Acid [4-[4-(3-cyano-benzyl)-piperazin-1-yl]-phenyl]-amide To a stirred solution of 4-[4-(3-cyano-benzyl)-piperazin-1-yl]-phenylamine (400 mg), 4'-isopropyl-6-methoxy-biphenyl-2-carboxylic acid (444 mg), HOBt (222 mg), and $Et_3N$ (166 mg) in $CH_2Cl_2$ (20 mL) was added at room temperature EDCl (315 mg) and the mixture was stirred at room temperature for 16 hours. The organic solution was then washed with water, with a saturated solution of $NaHCO_3$ and dried over $Na_2SO_4$. After filtration and evaporation of the filtrate, the residue was purified by flash chromatography eluting with $CH_2Cl_2/MeOH$ (95/5) to give the title compound (279 mg) as white crystals.

m.p.: 179° C.

Analysis for $C35H36N4O2(0.5H_2O)$ Calculated: C,75.92; H,6.73; N,10.12; Found: C,75.65; H,6.48; N,10.35%.

EXAMPLE 4
4'-Isopropyl-6-methyl-biphenyl-2-carboxylic Acid [4-[4-(3-cyano-benzyl)-piperazin-1-yl]-phenyl-amide To a stirred solution of 4-[4-(3-cyano-benzyl)-piperazin-1-yl]-phenylamine (400 mg), 4'-isopropyl-6-methyl-biphenyl-2-carboxylic acid (418 mg), HOBt (222 mg), and $Et_3N$ (166 mg) in $CH_2Cl_2$ (20 mL) was added at room temperature EDCl (315 mg) and the mixture was stirred at room temperature for 16 hours. The organic solution was then washed with water, with a saturated solution of $NaHCO_3$ and dried over $Na_2SO_4$. After filtration and evaporation of the filtrate, the residue was purified by flash chromatography eluting with $CH_2Cl_2/MeOH$ (98/2) and crystallized from AcOEt to give the title compound (304 mg) as white crystals.

m.p.: 137° C.

Analysis for $C35H36N4O$ Calculated: C,79.51; H,6.86; N,10.60; Found: C,79.31; H,6.36; N,10.78%.

EXAMPLE 5
6-Methyl-4'-trifluoromethyl-biphenyl-2-carboxylic Acid [4-[4-(3-cyano-benzyl)-piperazin-1-yl]-phenyl]-amide To a stirred solution of 4-[4-(3-cyano-benzyl)-piperazin-1-yl]-phenylamine (400 mg), 6-methyl-4'-trifluoromethyl-biphenyl-2-carboxylic acid (460 mg), HOBt (222 mg), and $Et_3N$ (166 mg) in $CH_2Cl_2$ (20 mL) was added at room temperature EDCl (315 mg) and the mixture was stirred at room temperature for 16 hours. The organic solution was then washed with water, with a saturated solution of $NaHCO_3$ and dried over $Na_2SO_4$. After filtration and evaporation of the filtrate, the residue was purified by flash chromatography eluting with $CH_2Cl_2/MeOH$ (98/2) and crystallized from AcOEt to give the title compound (122 mg) as white crystals.

m.p.: 192° C.

Analysis for $C33H29F3N4O$ Calculated: C,71.47; H,5.27; N,10.10; Found C,71.32; H,5.23; N,10.17%.

EXAMPLE 6

4'-Isopropyl-5-methyl-biphenyl-2-carboxylic Acid (4-{3-(3-methyl-[1,2,4]oxadiazol-5-yl)-benzyl]-piperazin-1-yl}-phenyl)-amide To a stirred solution of (4-{4-[3-(3-methyl-[1,2,4]oxadiazol-5-yl)-benzyl]-piperazin-1-yl}phenylamine (175 mg), 4'-isopropyl-5-methyl-biphenyl-2-carboxylic acid (127 mg), HOBt (87 mg), and Et$_3$N (67 mg) in CH$_2$Cl$_2$ (20 mL) was added at room temperature EDCl (124 mg) and the mixture was stirred at room temperature for 16 hours. The organic solution was then washed with water, with a saturated solution of NaHCO$_3$ and dried over Na$_2$SO$_4$. After filtration and evaporation of the filtrate, the residue was purified by flash chromatography eluting with CH$_2$Cl$_2$/MeOH (98/2) and crystallized from CH$_2$Cl$_2$/diisproyl ether to give the title compound (110 mg) as white crystals.

m.p.: 145–147° C.

Analysis for C37H39N5O2 Calculated: C,75.87; H,6.71; N,11.96; Found: C,75.79; H,7.02; N,11.81%.

Similarly prepared were:

EXAMPLE 7

5-Chloro-4'-isopropyl-biphenyl-2-carboxylic acid [4-[4-(3-cyano-benzyl)-piperazin-1-yl]-phenyl]-amide as white crystals (280 mg), m.p.: 188–190° C. from 5-chloro-4'-isopropyl-biphenyl-2-carboxylic acid (274 mg) and 4-[4-(3-cyano-benzyl)-piperazin-1-yl]-phenylamine (292 mg).

Analysis for C34H33ClN4O Calculated: C,74.37; H,6.06; N,10.20; Found: C,74.56; H,6.20; N,10.05%.

EXAMPLE 8

6-Methoxy-4'-trifluoromethyl-biphenyl-2-carboxylic acid [4-[4-(3-cyano-benzyl)-piperazin-1-yl]-phenyl]-amide as white crystals (225 mg), m.p.: 215–217° C. from 6-methoxy-4'-trifluoromethyl-biphenyl-2-carboxylic acid (150 mg) and 4-[4-(3-cyano-benzyl)-piperazin-1-yl]-phenylamine (150 mg).

Analysis for C33H29F3N4O2 (0.4H$_2$O) Calculated: C,68.60; H,5.20; N,9.70; Found C,68.50; H,5.19; N,9.56%.

EXAMPLE 9

5-Methyl-4'-trifluoromethyl-biphenyl-2-carboxylic acid [4-[4-(3-cyano-benzyl)-piperazin-1-yl]-phenyl]-amide as white crystals (240 mg), m.p.: 166–168° C. from 5-methyl-4'-trifluoromethyl-biphenyl-2-carboxylic acid (210 mg) and 4-[4-(3-cyano-benzyl)-piperazin-1-yl]-phenylamine (219 mg).

Analysis for C33H29F3N4O Calculated: C,71.47; H,5.27; N,10.10; Found: C,71.89; H,5.72; N,10.18%.

EXAMPLE 10

5-Chloro-4'-trifluoromethyl-biphenyl-2-carboxylic acid [4-[4-(3-cyano-benzyl)-piperazin-1-yl]-phenyl]-amide as white crystals (0.25 g), m.p.: 164–165° C. from 5-chloro-4'-trifluoromethyl-biphenyl-2-carboxylic acid (0.19 g) and 4-[4-(3-cyano-benzyl)-piperazin-1-yl]-phenylamine (0.18 g).

Analysis for C32H26ClF3N4O(0.5 H2O) Calculated: C,65.81; H,4.66; N,9.59; Found: C,65.49; H,4.79; N,9.75%.

Similarly prepared were:

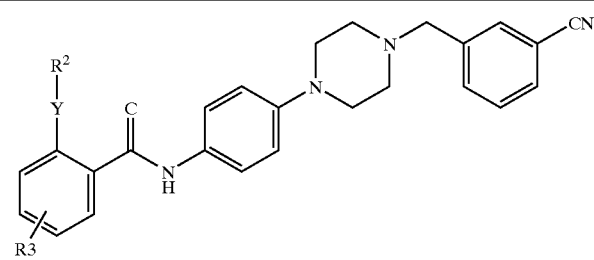

| Example | —Y—R$^2$ | R$^3$ | Molecular formula:<br>CHN calc:<br>CHN found:<br>or mass spec m/z | m.p. ° C. |
|---|---|---|---|---|
| Ex 11 | Ph | H | C31H28N4O(1.2 H$_2$O)<br>C, 75.34; H, 6.20; N, 11.34;<br>C, 75.07; H, 5.97; N, 11.24%. | 169–171 |
| Ex 12 | Ph | 5-OMe | C32H30N4O2<br>C, 76.47; H, 6.02; N, 11.15;<br>C, 76.71; H, 5.90; N, 10.95%. | 159–161 |
| Ex 13 | CF$_3$-⟨phenyl⟩- | 4-Cl | C32H26ClF3N4O<br>C, 66.84; H, 4.56; N, 9.74;<br>C, 66.31; H, 4.68; N, 9.75%. | 143–145 |
| Ex 14 | ⟨phenyl⟩-O-CH(CH$_3$)$_2$ | H | C31H28N4O2(0.5 H$_2$O)<br>C, 74.83; H, 5.87; N, 11.26;<br>C, 74.59; H, 5.68; N, 11.63%. | 133–134 |
| Ex 15 | ⟨phenyl⟩-(2-methyl-oxazol-5-yl) | H | C34H29N5O2(0.5 H$_2$O)<br>C, 74.43; H, 5.51; N, 12.76;<br>C, 74.07; H, 5.36; N, 12.70%. | 209–211 |

-continued

| Example | —Y—R² | R³ | Molecular formula: CHN calc: CHN found: or mass spec m/z | m.p. ° C. |
|---|---|---|---|---|
| Ex 16 | 4-isopropylphenyl | H | 515(M + 1) | 133–135 |
| Ex 17 | 4-CF₃-phenyl | 5-OMe | 571(M + 1) | 160–164 |
| Ex 18 | 4-CF₃-phenyl | 4-Me | 555(M + 1) | 120–124 |
| Ex 19 | 4-CF₃-phenyl | 4-OMe | 571(M + 1) | 151–155 |
| Ex 20 | 4-Et-phenyl | H | 501(M + 1) | 118–122 |
| Ex 21 | 4-MeO-phenyl | H | 503(M + 1) | 124–128 |
| Ex 22 | 3-CF₃-phenyl | H | 541(M + 1) | 117–121 |
| Ex 23 | 4-F-phenyl | H | 491(M + 1) | 200–202 |
| Ex 24 | 3,4-diMe-phenyl | H | 501(M + 1) | 140–144 |
| Ex 25 | 3,4-diMe-phenyl (alt) | H | 501(M + 1) | 72–76 |

| Example | —Y—R² | R³ | Molecular formula:<br>CHN calc:<br>CHN found:<br>or mass spec m/z | m.p. ° C. |
|---|---|---|---|---|
| Ex 26 | MeO—⟨phenyl with MeO⟩— | H | 533(M + 1) | 116–120 |

EXAMPLE 27

N-[4-[4-(3-Cyano-benzyl)-piperazin-1-yl]-phenyl]-2-(4-trifluoromethyl-benzyloxy)-benzamide To a stirred suspension of N-[4-[3-cyano-benzyl)-piperazin-1-yl]-phenyl]-2-hydroxy-benzamide (0.309 g) and K₂CO₃ (0.135 g) in acetone (10 mL) was added dropwise 4-trifluoromethyl-benzyf chloride (0.14 g) and the mixture was heated at reflux. After 16 hours, the mixture was cooled at room temperature, the salts were removed by filtration, washed with acetone and the filtrate was evaporated under reduced presssure. The residue was then purified by flash chromatography eluting with CH₂Cl₂/AcOEt (85/15) and the white solid obtained was recrystallized from EtOH to give the title compound (0.31 g) as white crystals.

m.p.: 190–191° C.

Analysis for C33H29F3N4O2 Calculated: C,69.46; H,5.12; N,9.82; Found C,69.49; H,5.03; N,9.80%.

EXAMPLE 28

N-[4-[4-(3-Cyano-benzyl)-piperazin-1-yl]-phenyl]-3-methoxy-2-(4-trifluoromethyl-benzyloxy)-benzamide To a stirred suspension of N-[4-[3-cyano-benzyl)-piperazin-1-yl]-phenyl]-2-hydroxy-3-methoxy-benzamide (0.33 g) and K₂CO₃ (0.134 g) in acetone (15 mL) was added dropwise 4-trifluoromethyl-benzyl chloride (0.146 g) and the mixture was heated at reflux. After 16 hours, the mixture was cooled to room temperature, the salts were removed by filtration, washed with acetone and the filtrate was evaporated under reduced presssure. The residue was then crystallized from EtOH to give the title compound (0.29 g) as pale yellow crystals.

m.p.: 118–119.5° C.

Analysis for C34H31F3N4O3 Calculated: C,67.99; H,5.20; N,9.33; Found C,67.98; H,5.07; N,9.32%.

Similarly prepared were

| Example | Y—R² | R³ | Molecular formula:<br>CHN calc:<br>CHN found: | m.p. ° C. |
|---|---|---|---|---|
| Ex 29 | F—⟨phenyl⟩—CH₂O— | 3-OMe | C33H31FN4O3<br>C, 71.98; H, 5.67; N, 10.18;<br>C, 72.50: H, 5.68; N, 10.06%. | 118–120 |

-continued

[Structure with R², Y, C(=O)NH-phenyl-piperazine-CH₂-phenyl-CN, with R³]

| Example | Y—R² | R³ | Molecular formula:<br>CHN calc:<br>CHN found: | m.p. ° C. |
|---|---|---|---|---|
| Ex 30 | [phenyl-CH₂CH₂-O-] | 3-OMe | C34H34N4O3<br>C, 74.70; H, 6.27; N, 10.25;<br>C, 74.73; H, 6.37; N, 10.10%. | 140–142 |
| Ex 31 | [cyclohexyl-CH₂CH₂-O-] | 3-OMe | C34H40N4O3<br>C, 73.88; H, 7.29; N, 10.14;<br>C, 74.30; H, 6.91; N, 9.97%. | 102–104 |
| Ex 32 | [cyclohexyl-CH₂CH₂-O-] | H | C33H38N4O2<br>C, 75.83; H, 7.33; N, 10.72;<br>C, 76.34; H, 7.19; N, 10.52%. | 119–121 |
| Ex 33 | [phenyl-CH₂CH₂-O-CH₂-] | 3-OMe | C35H36N4O3<br>C, 74.98; H, 6.47; N, 9.99;<br>C, 74.57; H, 6.42; N, 9.70%. | 134–136 |

EXAMPLE 34

4'-Trifluoromethyl-biphenyl-2-carboxylic Acid [4-[4-(3-cyano-benzyl)-piperazin-1-yl]-phenyl]-amide-(Method 2)

To a solution of 4'-trifluoromethyl-biphenyl-2-carboxylic acid (4-piperazin-1-yl-phenyl)-amide (0.58 g) in CH₂Cl₂ (35 mL) containing Et₃N (0.152 g) was added 3-cyano-benzyl bromide (0.267 g) and the mixture was heated at reflux for 2 hours. The solution was washed with water, dried over Na₂SO₄, filtered and evaporated. The residue was purified by flash chromatography eluting with CH₂Cl₂/MeOH (98/2) and the solid obtained was recrystallized from MeOH/H₂O to give the title compound (0.67 g) as white crystals.

m.p.: 153–155° C.

Analysis for C32H27F3N4O Calculated: C,71.10; H,5.03 N,10.36; Found: C,70.86; H,4.98; N,10.27%.

EXAMPLE 35

N-4-[4-(3-Cyano-benzyl)-piperazin-1-yl]-phenyl]-2-(4-fluoro-benzyloxy)-benzamide To a solution of 2-(4-fluoro-benzyloxy)-N-(4-piperazin-1-yl-phenyl)-benzamide (0.31 g) in CH₂Cl₂ (10 mL) containing Et₃N (84 mg) was added 3-cyano-benzyl bromide (0.147 g) and the mixture was heated at reflux for 2 hours. The solution was washed with water, dried over Na₂SO₄, filtered and evaporated. The residue was crystallized from diisopropy ether to give the title compound (0.21 g) as white crystals.

m.p.: 114–116° C.

Analysis for C32H29FN4O2 C,73.83; H,5.61; N,10.76; C,74.10; H,5.89; N,10.68%.

EXAMPLE 36

4'-Trifluoromethyl-biphenyl-2-carboxylic Acid [3-[4-(3-cyano-benzyl)-piperazin-1-yl]-phenyl]-amide To a solution of 4'-trifluoromethyl-biphenyl-2-carboxylic acid (3-piperazin-1-yl-phenyl)-amide (0.5 g) in acetone (20 mL) containing K₂CO₃ (0.19 g) was added 3-cyano-benzyl bromide (0.23 g) and the mixture was heated at reflux for 2 hours. The solution was cooled at room temperature and the salts were removed by filtration, washed with acetone and the filtrate was evaporated under reduced pressure. The residue was purified by crystallizatiori from AcOEt to give the title compound (0.17 g) as white crystals.

m.p.: 170–172° C.

Analysis for C32H27F3N4O Calculated: C,71.10; H,5.03; N,10.36; Found: C,70.69; H,5.15; N,10.18%.

EXAMPLE 37

4'-Trifluoromethyl-biphenyl-2-carboxylic Acid [4-(4-carbamoylrmethyl-piperazin-1-yl)-phenyl]-amide To a solution of 4'-trifluoromethyl-biphenyl-2-carboxylic acid (4-piperazin-1-yl-phenyl)-amide (0.31 g) in acetone (10 mL) containing K₂CO₃ (0.31 g) was added 2-bromo-acetamide (0.124 g) and the mixture was heated at reflux for 3 hours. After cooling at room temperature the salts were removed by filtration, washed with acetone and the filtrate was evaporated under reduced pressure. The residue was purified by flash chromatography eluting with CH₂Cl₂/MeOH (95/5) and the solid obtained was recrystallized from EtOH to give the title compound (0.23 g) as white crystals.

m.p.: 226–228° C.

Analysis for C26H25F3N4O2 Calculated: C,64.72; H,5.22; N,11.61; Found: C,64.69; H,5.45; N,11.59%.

EXAMPLE 38

4'-Isopropyl-4-methoxy-biphenyl-2-carboxylic Acid [4-(4-carbamoylmethyl-piperazin-1-yl)-phenyl]-amide To a solution of 4'-isopropyl-6-methoxy-biphenyl-2-carboxylic acid (4-piperazin-1-yl-phenyl)-amide (214 mg) in acetone (20 mL) containing $K_2CO_3$ (206 mg) was added 2-bromo-acetamide (100 mg) and the mixture was heated at reflux for 16 hours. After cooling at room temperature the salts were removed by filtration, washed with acetone and the filtrate was evaporated under reduced pressure. The residue was purified by flash chromatography eluting with $CH_2Cl_2$/MeOH (92/8) and the solid obtained was recrystallized from $CH_2Cl_2$/diisopropyl ether to give the title compound (120 mg) as white crystals.

m.p.: 207–209° C.

Analysis for $C_{29}H_{34}N_4O_3$ Calculated: C,71.58; H,7.04; N,11.51; Found: C,71.68; H,6.47; N,11.44%.

EXAMPLE 39

4'-Isopropyl-6-methyl-biphenyl-2-carboxylic Acid [4-(4-carbamoylmethyl-piperazin-1-yl)-pheny]-amide To a solution of 4'-isopropyl-6-methyl-biphenyl-2-carboxylic acid (4-piperazin-1-yl-phenyl)-amide (206 mg) in acetone (20 mL) containing $K_2CO_3$ (206 mg) was added 2-bromo-acetamide (100 mg) and the mixture was heated at reflux for 16 hours. After cooling at room temperature the salts were removed by filtration, washed with acetone and the filtrate was evaporated under reduced pressure. The residue was purified by flash chromatography eluting with $CH_2Cl_2$/MeOH (93/7) and the solid obtained was recrystallized from $CH_2Cl_2$/diisopropyl ether to give the title compound (190 mg) as white crystals.

m.p.: 181–183° C.

Analysis for $C_{29}H_{34}N_4O_2$ Calculated: C,74.01; H,7.28; N,11.91; Found: C,73.87; H,6.69; N,11.84%.

Similarly prepared were:

EXAMPLE 40

6-Methyl-4'-trifluoromethyl-biphenyl-2-carboxylic acid [4-(4-carbamoylmethyl-piperazin-1-yl)-phenyl]-amide as white crystals (100 mg), m.p.: 196–198° C. from 6-methyl-4'-trifluoromethyl-biphenyl-2-carboxylic acid (4-piperazin-1-yl-phenyl)-amide (220 mg) and 2-bromo-acetamide (100 mg).

Analysis for $C_{27}H_{27}F_3N_4O_2(0.25H_2O)$ Calculated: C,64.73; H,5.53; N,11.18; Found: C,64.44; H,4.93; N,10.98%.

EXAMPLE 41

4'-Trifluoromethyl-biphenyl-2-carboxylic acid [4-(4-cyanomethyl-piperazin-1-y]-phenyl]-amide as white crystals (1.3 g), m.p.: 244–246° C. from 4'-trifluoromethyl-biphenyl-2-carboxylic acid (4-piperazin-1-yl-phenyl)-amide (2.12 g) and chloro-acetonitrile (396 mg).

Analysis for $C_{26}H_{23}F_3N_4O$ $(0.25H_2O)$ Calculated: C,66.59; H,5.05; N,11.95; Found: C,66.51; H,4.89; N,11.81%.

EXAMPLE 42

4'-Trifluoromethyl-biphenyl-2-carboxylic acid [4-(4-ethoxycarbonylmethyl-piperazin-1-yl)-phenyl)-amide as white crystals (5.1 g), m.p.: 167–169° C. from 4'-trifluoromethyl-biphenyl-2-carboxylic acid (4-piperazin-1-yl-phenyl)-amide (4.25 g) and bromo-acetic acid ethyl ester (1.83 g).

Analysis for $C_{28}H_{28}F_3N_3O_3$ Calculated: C,65.74; H,5.52; N,8.21 Found: C,65.76; H,5.09; N,8.16%.

EXAMPLE 43

4'-Trifluoromethyl-biphenyl-2-carboxylic acid [4-(4-(2-ethoxy-ethyl)-piperazin-1-yl]-phenyl]-amide as white crystals (210 mg), m.p.: 176–178° C. from 4'-trifluoromethyl-biphenyl-2-carboxylic acid (4-piperazin-1-yl-phenyl)-amide (318 mg) and 1-bromo-2-ethoxy-ethane (126 mg).

Analysis for $C_{28}H_{30}F_3N_3O_2$ Calculated: C,67.59; H,6.08; N,8.45; Found: C,67.63; H,6.05; N,8.49%.

EXAMPLE 44

4'-Trifluoromethyl-biphenyl-2-carboxylic acid [4-(4-(3-hydroxy-propyl)-piperazin-1-yl]-phenyl]-amide as white crystals (160 mg), m.p.: 208–210° C. from 4'-trifluoromethyl-biphenyl-2-carboxylic acid (4-piperazin-1-yl-phenyl)-amide (318 mg) and 3-bromo-propan-1-ol (125 mg).

Analysis for $C_{27}H_{28}F_3N_3O_2(0.5H_2O)$ Calculated: C,65.84; H,5.93; N,8.53; Found: C,65.66; H,6.23; N,8.40%.

EXAMPLE 45

4'-Trifluoromethyl-biphenyl-2-carboxylc acid [4-(4-(4,4,4-trifluoro-butyl)-piperazin-1-yl)-phenyl]-amide as white crystals (240 mg), m.p.: 198–200° C. from 4'-trifluoromethyl-biphenyl-2-carboxylic acid (4-piperazin-1-yl-phenyl)-amide (297 mg) and 4-bromo-1,1,1-trifluoro-butane (143 mg).

Analysis for $C_{28}H_{27}F_6N_3O$ $(0.5H_2O)$ Calculated: C,61.76; H,5.18; N,7.72; Found: C,61.53; H,4.88; N,7.55%.

EXAMPLE 46

4'-Trifluoromethyl-biphenyl-2-carboxylic acid f4-(4-(3-methyl-but-2-enyl)-piperazin-1-yl]-phenyl]-amide as white crystals (180 mg), m.p.: 203–205° C. from, 4'-trifluoromethyl-biphenyl-2-carboxylic acid (4-piperazin-1-yl-phenyl)-amide (318 mg) and 1-bromo-3-methyl-but-2-ene (122 mg).

Analysis for $C_{29}H_{30}F_3N_3O$ $(0.4H_2O)$ Calculated: C,69.56; H,6.20; N,8.39; Found: C,69.34; H,5.62; N,8.55%.

EXAMPLE 47

4'-Trifluoromethyl-biphenyl-2-carboxylic acid [4-(4-(3-cyano-4-fluoro-benzyl)-piperazin-1-yl)-phenyl-amide as white crystals (440 mg), m.p.: 168–170° C. from 4'-trifluoromethyl-biphenyl-2-carboxylic acid (4-piperazin-1-yl-phenyl)-amide (425 mg) and 3-cyano4-fluoro-benzyl bromide (214 mg).

Analysis for $C_{32}H_{26}F_4N_4O$ Calculated: C,68.81; H,4.69; N,10.03; Found: C,68.83; H,4.55; N, 9.98%.

EXAMPLE 48

4'-Trifluoromethyl-biphenyl-2-carboxylic acid [4-(4-(3,4-methylenedioxy-benzyl)-piperazin-1-yl)-phenyl]-amide as white crystals (180 mg), m.p.: 189–191° C. from 4'-trifluoromethyl-biphenyl-2-carboxylic acid (4-piperazin-1-yl-phenyl)-amide (318 mg) and 3,4-methylenedioxy-benzyl chloride (140 mg).

Analysis for $C_{32}H_{28}F_3N_3O_3$ Calculated: C,68.68; H,5.04; N,7.51; Found: C,68.44; H,5.04; N,7.54%.

EXAMPLE 49

4'-Trifluoromethyl-biphenrryl-2-carboxylic acid [4-(4-(3-nitro-benzyl)-piperazin-1-yl)-phenyl]-amide as pale yellow crystals (900 mg), m.p.: 152–154° C. from 4'-trifluoromethyl-biphenyl-2-carboxylic acid (4-piperazin-1-yl-phenyl)-amide (1.06 g) and 3-nitro-benzyl bromide (538 mg).

Analysis for C31 H27F3N4O3 Calculated: C,66.42; H,4.85; N,9.99; Found: C,66.02; H,5.03; N,9.95%.

EXAMPLE 50

4'-Trifluoromethyl-biphenyl-2-carboxylic acid {4-[4-(3-carbamoyl-benzyl)-piperazin-1-yl]-phenyl)amide as white cystals (1.5 g), m.p.: 199–201° C. from 4'-trifluoromethyl-biphenyl-2-carboxylic acid (4-piperazin-1-yl-phenyl)-amide (1.7 g) and 3-chloromethyl-benzamide (676 mg).

Analysis for C32H29F3N4O2 Calculated: C,68.81; H,5.23; N,10.03; Found: C,68.84; H,5.52; N,9.99%.

Similarly prepared were:

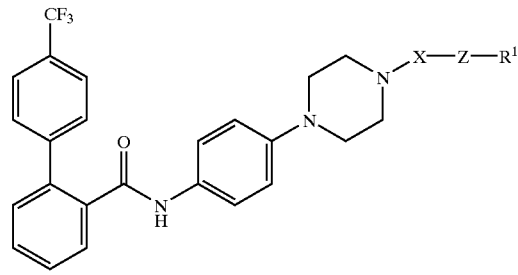

| Example | —X—Z—R¹ | Molecular formula:<br>CHN calc:<br>CHN found: | m.p. ° C. |
|---|---|---|---|
| Ex 51 | Me—O—<br>=<br>—CH₂ | C32H30F3N3O2(1 H₂O)<br>C, 68.19; H, 5.72; N, 7.46;<br>C, 68.39; H, 6.03; N, 7.07%. | 168–170 |
| Ex 52 | F—⬡—CH₂ | C31H27F4N3O<br>C, 69.78; H, 5.10; N, 7.88;<br>C, 69.37; H, 5.17; N, 7.84%. | 198–200 |
| Ex 53 | F-⬡—CH₂ (meta) | C31H27F4N3O(0.6 H₂O)<br>C, 68.40; H, 5.22; N, 7.72;<br>C, 68.39; H, 5.14; N, 7.70%. | 189–190.5 |
| Ex 54 | ⬡—CH₂ | C31H28F3N3O(0.2 H₂O)<br>C, 71.72; H, 5.51; N, 8.09;<br>C, 71.43; H, 5.51; N, 8.02%. | 191–193 |
| Ex 55 | MeO₂C-⬡—CH₂ | C33H30F3N3O3<br>C, 69.10; H, 5.27; N, 7.33;<br>C, 68.70; H, 5.13; N, 7.10%. | 190–192 |
| Ex 56 | pyridyl-CH₂ (4-) | C30H27F3N4O<br>C, 69.76; H, 5.27; N, 10.85;<br>C, 69.67; H, 5.28; N, 10.86%. | 194–196 |
| Ex 57 | pyridyl-CH₂ (2-) | C30H27F3N4O(0.5 H₂O)<br>C, 68.56; H, 5.37; N, 10.66;<br>C, 68.46; H, 5.21; N, 10.58%. | 168–170 |
| Ex 58 | pyrimidinyl-CH₂ | C29H26F3N5O<br>C, 67.30; H, 5.06; N, 13.53;<br>C, 66.84; H, 5.07; N, 13.30%. | 183–185 |

-continued

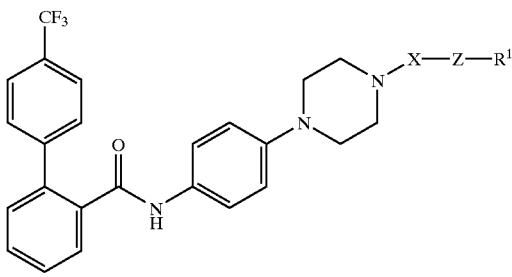

| Example | —X—Z—R¹ | Molecular formula:<br>CHN calc:<br>CHN found: | m.p. ° C. |
|---|---|---|---|
| Ex 59 | thiazol-2-ylmethyl | C28H25F3N4OS(0.25 H₂O)<br>C, 63.80; H, 4.88; N, 10.63;<br>C, 63.69; H, 4.97; N, 10.65%. | 187–189 |
| Ex 60 | 1-methylimidazol-2-ylmethyl | C29H28F3N5O<br>C, 67.04; H, 5.43; N, 13.48;<br>C, 66.52; H, 5.64; N, 13.28%. | 118–120 |

EXAMPLE 61
4'-Isopropyl-6-methyl-biphenyl-2-carboxylic Acid (4-(4-(3-(3-methyl-1,2,4]oxadiazol-5-yl)-benzyl)-piperazine-1-yl)-phenyl)-amide To a solution of 4'-isopropyl-6-miethyl-biphenyl-2-carboxylic acid (4-piperazin-1-yl-phenyl)-amide (309 mg) in 1,2-dichloroethane (20 mL) was added 3-(3-methyl-[1,2,4]oxadiazol-5-yl)-benzaldehyde (154 mg) and acetic acid (67 mg). The solution was cooled at 0° C. and sodium triacetoxy borohydride (317 mg) was added portionwise and the mixture was stirred at room temperature for 16 hours. The solution was then washed with a saturated solution of NaHCO₃, with brine, dried over Na₂SO₄, filtered and evaporated under reduced pressure. The residue was purified by flash chromatography eluting with CH₂Cl₂/MeOH (98/2) and the solid obtained was recrystallized from CH₂Cl₂/hexane to give the title compound (140 mg) as white crystals m.p.: 74° C.

Analysis for C37H39N5O2(0.5H₂O) Calculated: C,74.72; H,6.78; N,11.78; Found: C,74.39; H,6.74; N,11.73%.

EXAMPLE 62
4'-Trifluormethyl-biphenyl-2-carboxylic Acid [4-(4-(1H-pyrrol-2-ylmethyl)-piperazin-1-yl)-phenyl)-amide To a solution of 4'-trifluoromethyl-biphenyl-2-carboxylic acid (4-piperazin-1-yl-phenyl)-amide (310 mg) in 1,2-dichloroethane (20 mL) was added 1H-pyrrole-2-carboxaldehyde (95 mg) and acetic acid (67 mg). The solution was cooled at 0° C. and sodium triacetoxy borohydride (317 mg) was added portionwise and the mixture was stirred at room temperature for 16 hours. The solution was then washed with a saturated solution of NaHCO₃, with brine, dried over Na₂SO₄, filtered and evaporated under reduced pressure. The residue was purified by flash chromatography eluting with CH₂Cl₂/MeOH (95/5) and the solid obtained was recrystallized from EtOH to give the title compound (180 mg) as white crystals.
m.p.: 191–193° C.

Analysis for C29H27F3N4O Calculated: C,69.04; H,5.39; N,11.10; Found: C,69.56; H,5.80; N,11.06%.

EXAMPLE 63
4'-Isopropyl-5-methyl-biphenyl-2-carboxylic Acid [4-(4-(1H-pyrrol-2-ylmethyl)-25 piperazin-1-yl)-phenyl]-amide To a solution of 4'-isopropyl-5-methyl-biphenyl-2-carboxylic acid (4-piperazin-1-yl-phenyl)-amide (290 mg) in 1,2-dichloroethane (20 mL) was added 1H-pyrrole-2-carboxaldehyde (68 mg) and acetic acid (67 mg). The solution was cooled at 0° C. and sodium triacetoxy borohydride (317 mg) was added portionwise and the mixture was stirred at room temperature for 16 hours. The solution was then washed with a saturated solution of NaHCO₃, with brine, dried over Na₂SO₄, filtered and evaporated under reduced pressure. The residue was purified by flash chromatography eluting with CH₂Cl₂/MeOH (98/2) and the solid obtained was recrystallized from MeOH to give the title compound (60 mg) as white crystals.
m.p.: 185–187° C.

Analysis for C32H36N4O Calculated: C,78.02; H,7.36; N, 11.37; Found: C,78.35; H,7.11; N,11.27%.

EXAMPLE 64
5-Methyl-4'-trifluoromethyl-biphenyl-2-carboxylic Acid [4-(4-(1H-pyrrol-2-ylmethyl)-piperazin-1-yl)-phenyl]-amide To a solution of 5-methyl-4'-trifluoromethyl-biphenyl-2-carboxylic acid (4-piperazin-1-yl-phenyl)-amide (329 mg) in 1,2-dichloroethane (20 mL) was added 1H-pyrrole-2-carboxaldehyde (86 mg) and acetic acid (54 mg). The solution was cooled at 0° C. and sodium triacetoxy borohydride (238 mg) was added portionwise and the mixture was stirred at room temperature for 16 hours. The solution was then washed with a saturated solution of NaHCO₃, with brine, dried over Na₂SO₄, filtered and evaporated under reduced pressure. The residue was purified by flash chromatography eluting with CH₂Cl₂/MeOH (95/5) and the oily residue obtained was crystallized from diisopropyl ether to give the title compound (210 mg) as white crystals.
m.p.: 196–198° C.

EXAMPLE 65

Analysis for C30H29F3N4O(0.5H$_2$O) Calculated: C,68.30; H,5.73; N,10.62; Found: C,68.05; H,6.03; N, 10.36%.
Similarly prepared were:

EXAMPLE 65

4'-Trifluoromethyl-biphenyl-2-carboxylic acid [4-(4-propyl-piperazin-1-yl)-phenyl]-amide as white crystals (160 mg), m.p .: 207–209° C. from 4'-trifluoromethyl-biphenyl-2-carboxylic acid (4-piperazin-1-yl-phenyl)-amide (0.31 g) and propionaldehyde (64 mg).

Analysis for C27H28F3N3O Calculated: C,69.36; H,6.04; N,8.99; Found; C,69.47; H,6.12; N,8.86%.

EXAMPLE 66

4'-Trifluoromethyl-biphenyl-2-carboxylic acid [4-(4-(3-acetyl-benzyl)-piperazin-1-yl)-phenyl]-amide as white crystals (235 mg), m.p.: 181–183° C. from 4'-trifluoromethyl-biphenyl-2-carboxylic acid (4-piperazin-1-yl-phenyl)-amide (0.31 g) and 3-acetyl-benzaldehyde (122 mg).

Analysis for C33H30F3N3O2(0.25H$_2$O) Calculated: C,70.51; H,5.47; N,7.48; Found: C,70.41; H,5.12; N,7.40%.

EXAMPLE 67

4'-Trifluoromethyl-biphenyl-2-carboxylic acid [4-(4-furan-2-ylmethyl-piperazin-1-yl)-phenyl]-amide as a pale yellow solid (180 mg), m.p.: 173–175° C. from 4'-trifluoromethyl-biphenyl-2-carboxylic acid (4-piperazin-1-yl-phenyl)-amide (0.31 g) and furan-2-carboxaldehyde (106 mg).

Analysis for C29H26F3N3O2 Calculated: C,68.90; H,5.18; N,8.31; Found: C,69.00; H,5.31; N,8.17%.

EXAMPLE 68

4'-Isopropyl-6-methoxy-biphenyl-2-carboxylic acid [4-(4-(1H-pyrrol-2-ylmethyl)-piperazin-1-yl)-phenyl]-amide as white crystals (230 mg), m.p.: 195–197° C. from 4'-isopropyl-6-methoxy-biphenyl-2-carboxylic acid (4-piperazin-1-yl-phenyl)-amide (0.3 g) and 1H-pyrrole-2-carboxaldehyde (68.5 mg).

Analysis for C32H36N4O2 Calculated: C,75.56; H,7.13; N,11.01; Found: C,75.79; H,7.16; N,11.03%.

EXAMPLE 69

4'-Trifluoromethyl-biphenyl-2-carboxylic acid [4-(4-(41-methyl-1H-pyrrol-2-ylmethyl)-piperazin-1-yl)-phenyl]-amide as white crystals (150 mg), m.p.: 177–179° C. from 4'-trifluoromethyl-biphenyl-2-carboxylic acid (4-piperazin-1-yl-phenyl)-amide (0.31 g) and 1-methyl-1H-pyrrole-2-carboxaldehyde (109 mg).

Analysis for C30H29F3N4O (1H$_2$O) Calculated: C,67.15; H,5.82; N,10.44; Found: C,67.45; H,5.70; N,10.51%.

EXAMPLE 70

4'-Trifluoromethyl-biphenyl-2-carboxylic acid [4-(4-thiophen-2-ylmethyl-piperazin-1-yl)-phenyl]-amide as a yellow solid (150 mg), m.p.: 181–183° C. from 4'-trifluoromethyl-biphenyl-2-carboxylic acid (4-piperazin-1-yl-phenyl)-amide (0.31 g) and thiophene-2-carboxaldehyde (126 mg).

Analysis for C29H26F3N3OS (1.25H$_2$O) Calculated: C,64.01; H,5.28; N,7.72; Found: C,64.05; H,5.04; N,7.72%.

EXAMPLE 71

4'-Trifluoromethyl-biphenyl-2-carboxylic acid {4-[4-(1H-pyrazole-3-ylmethyl)-piperazine-1-yl]-phenyl}-amide as white crystals (210 mg), m.p.: 194–196° C. from 4'-trifluoromethyl-biphenyl-2-carboxylic acid (4-piperazin-1-yl-phenyl)-amide (0.31 g) and 1H-pyrazole-3-carboxaldehyde (79 mg).

MS: m/z 506(M+1).

EXAMPLE 72

4'-Trifluoromethyl-biphenyl-2-carboxylic acid (4-(4-thiophen-3-ylmethyl-piperazin-1-yl)-phenyli-amide as white crystals (170 mg), m.p.: 187–189° C. from 4'-trifluoromethyl-biphenyl-2-carboxylic acid (4-piperazin-1-yl-phenyl)-amide (0.31 g) and thiophene-3-carboxaldehyde (112 mg).

Analysis for C29H26F3N3OS Calculated: C,66.78; H,5.02; N,8.06; Found: C,67.10; H,5.40; N,8.01%.

EXAMPLE 73

4'-Trifluoromethyl-biphenyl-2-carboxylic acid {4-[4-(5-fluoro-1H-indol-3-ylmethyl)-piperazin-1-yl]-phenyl}-amide as white crystals (190 mg), m.p.: 168–170° C. from 4'-trifluoromethyl-biphenyl-2-carboxylic acid (4-piperazin-1-yl-phenyl)-amide (318 mg) and 5-fluoro-1H-indole-3-carboxaldehyde (135 mg).

Analysis for C33H28F4N4O (0.5H$_2$O) Calculated: C,68.15; H,5.03; N,9.63; Found: C,67.97; H,5.09; N,9.43%.

EXAMPLE 74

4'-Isopropyl-6-methoxy-biphenyl-2-carboxylic acid (4-(4-(3-(3-methyl-[1,2,4]oxadiazol-5-yl)-benzyl)-piperazine-1-yl)-phenyl)-amide as white crystals (300 mg), m.p.: 180–182° C. from 4'-isopropyl-6-methoxy-biphenyl-2-carboxylic acid (4-piperazin-1-yl-phenyl)-amide (0.32 g) and 3-(3-methyl-[1 ,2,4]oxadiazol-5-yl)-benzaldehyde (154 mg).

Analysis for C37H39N5O3(0.5H$_2$O) Calculated: C,72.76; H,6.60; N,11.47; Found: C 72.80; H,6.59; N,11.31%.

EXAMPLE 75

4'-Trifluoromethyl-biphenyl-2-carboxylic acid (4-{4-[3-(5-trifluoromethyl-[1,2,4]oxadiazol-3-yl)-benzyl]-piperazin-1-yl}-phenyl)-amide as white crystals (240 mg), m.p.: 188–190° C. from 4'-trifluoromethyl-biphenyl-2-carboxylic acid (4-piperazin-1-yl-phenyl)-amide (0.31 g) and 3-(5-trifluoromethyl-[1,2,4]oxadiazol-3-yl)-benzaldehyde (198 mg).

Analysis for C34H27F6N5O2 Calculated: C,62.67; H,4.18; N,10.75; Found: C,62.09; H,4.65; N,10.56%.

EXAMPLE 76

(4-{4-[(4'-Trifluoromethyl-biphenyl-2-carbonyl)-amino]-phenyl}-piperazin-1-yl)-acetic Acid To a solution of 4'-trifluoromethyl-biphenyl-2-carboxylic acid [4-(4-ethoxycarbonylmethyl-piperazin-1-yl)-phenyl]-amide (4.6 g) in EtOH (80 mL) was added 1N sodium hydroxide and the mixture was stirred under reflux for 2 hours. The solution was cooled at room temperature, acidified with concentrated HCl and evaporated to dryness. The solid residue was purified by flash chromatography eluting with CH$_2$Cl$_2$/MeOH/Et$_3$N (70/30/0.2) and the solid was recrystallized from EtOH to give the title compound (4.2 g) as white crystals.

m.p.: 195–197° C.

EXAMPLE 77
4'-Trifluoromethyl-biphenyl-2-carboxylic Acid [4-(4{[(biphenyl-3-ylmethyl)-carbamoyl]-methyl}piperazin-1-yl)-phenyl]-amide To a stirred solution of (4-{4-[(4'-trifluoromethyl-biphenyl-2-carbonyl)-amino]-phenyl}-piperazin-1-yl)-acetic acid (241 mg), biphenyl-3-yl-methylamine (95 mg), HOBt (87 mg), and Et₃N (202 mg) in CH₂Cl₂ (20 mL) was added EDCl (125 mg) and the mixture was stirred at room temperature for 16 hours. The organic solution was then washed with water, with a saturated solution of NaHCO₃ and dried over Na₂SO₄. After filtration and evaporation of the filtrate, the residue was purified by flash chromatography eluting with CH₂Cl₂/MeOH (97/3) and the solid obtained was recrystallized from EtOH to give the title compound (180 mg) as white crystals.

m.p.: 165–167° C.

Analysis for C39H35F3N4O2 Calculated: C,72.21; H,5.44; N,8.64; Found: C,71.94; H,5.66; N,8.53%.

EXAMPLE 78
3-(4-{4-[(4'-Trifluoromethyl-biphenyl-2-carbonyl)-amino]-phenyl}-piperazin-1-ylmethyl)-benzoic Acid To a solution of 4'-trifluoromethyl-biphenyl-2-carboxylic acid [4-[4-(3-carbomethoxy-benzyl)-piperazin-1-yl]-phenyl]-amide (1.6 g) in EtOH (100 mL) was added 1N sodium hydroxide (5.6 mL) and the mixture was stirred under reflux for 16 hours. The solution was cooled at room temperature and acidified with 1N hydrochloric acid (5.6 mL). The white precipitate obtained was filtered and recristallized from EtOH to give the title compound (1.4 g) as white crystals. m.p.: 225–227° C.

EXAMPLE 79
4'-Trifluoromethyl-biphenyl-2-carboxylic Acid (4-{4-[3-(2,2,2-trifluoro-ethylcarbamoyl)-benzyl]-piperazin-1-yl}-phenyl)-amide To a stirred solution of 3-(4-{4-[(4'-trifluoromethyl-biphenyl-2-carbonyl)-amino)-phenyllpiperazin-1-ylmethyl)-benzoic acid (279 mg), 2,2,2-trifluoro-ethylamine (74 mg), HOBt (85 mg), and Et₃N (63 mg) in CH₂Cl₂ (10 mL) was added EDCl (125 mg) and the mixture was stirred at room temperature for 48 hours. The organic solution was then washed with water, with a saturated solution of NaHCO₃ and dried over Na₂SO₄. After filtration and evaporation of the filtrate, the residue was purified by flash chromatography eluting with CH₂Cl₂/MeOH (97/3) and the solid obtained was recrystallized from CH2Cl2/diisopropyl ether to give the title compound (190 mg) as white crystals.

m.p.: 205–207° C.

Analysis for C34H30F6N4O2 Calculated: C,63.75; H,4.72; N,8.75; Found: C,63.65; H,4.95; N,8.63%.

EXAMPLE 80
4'-Trifluoromethyl-biphenyl-2-carboxylic Acid [4-[4-(3-cyano-benzoyl)-piperazin-1-yl]-phenyl]-amide To a stirred solution of 4'-trifluoromethyl-biphenyl-2-carboxylic acid (4-piperazin-1-yl-phenyl)-amide (0.318 g) in CH₂Cl₂ (15 mL) containing Et₃N (79 mg) was added dropwise 3-cyano-benzoyl chloride (0.129 g) and the mixture was stirred at room temperature for 1 hour. The solution was then washed with water, with brine, dried over Na₂SO₄, filtered and evaporated. The residue was then purified by flash chromatography eluting with CH₂Cl₂/AcOEt (80/20) and the solid obtained was recrystallized from AcOEt to give the title compound (0.29 g) as white crystals.

m.p, : 178.5–180° C.

Analysis for C32H25F3N4O2 Calculated: C,69.31; H,4.54; N,10.10; Found: C,69.49; H,4.63; N,10.08%.

EXAMPLE 81
4'-Trifluoromethyl-biphenyl-2-carboxylic Acid [4-(4-acetyl-piperazin-1-yl)-phenyl]-amide A solution of 4'-trifluoromethyl-biphenyl-2-carboxylic acid (4-piperazin-1-yl-phenyl)-amide (212 mg) in acetic anhydride (10 mL) was stirred at room temperature for 16 hours. The solution was evaporated under reduced pressure, and the residue was dissolved in CH₂Cl₂ and washed with a saturated solution of NaHCO₃, with brine, dried over Na₂SO₄, filtered and evaporated. The oily residue was crystallized from AcOEt to give the title compound (130 mg) as white crystals.

m.p.: 175–176.5° C.

Analysis for C26H24F3N3O2 Calculated: C,66.80; H,5.17; N,8.99; Found: C,66.69; H,5.15; N,8.87%.

EXAMPLE 82
4'-Trifluoromethyl-biphenyl-2-carboxylic Acid [4-[4-(3-cyano-benzenesulfonyl)-piperazin-1-yl]-phenyl]-amide To a stirred solution of 4'-trifluoromethyl-biphenyl-2-carboxylic acid (4-piperazin-1-yl-phenyl)-amide (0.318 g) in CH₂Cl₂ (20 mL) containing. Et₃N (90 mg) was added dropwise 3-cyano-benzenesulfonyl chloride (0.179 g) and the mixture was stirred at room temperature for 48 hours. The solution was then washed with water, with brine, dried over Na₂SO₄, filtered and evaporated. The residue was then purified by flash chromatography eluting with CH₂Cl₂ to give the title compound (0.39 g) as a white solid.

m.p.: 223° C.

Analysis for C31H25F3N4O3S(0.5H₂O) Calculated: C,62.10; H,4.37; N,9.34; Found: C,62;03; H,4.55; N,9.11%.

EXAMPLE 83
4'-Trifluoromethyl-biphenyl-2-carboxylic Acid [4-(4-methanesulfonyl-piperazin-1-yl)-phenyl]-amide To a solution of 4'-trifluoromethyl-biphenyl-2-carboxylic acid (4-piperazin-1-yl-phenyl)-amide (318 mg) in CH₂Cl₂ (10 mL) containing Et₃N (91 mg) was added methanesulfonyl chloride (70 μL) and the mixture was stirred at room temperature for 1 hour. The solution was washed with water, with brine and dried over Na₂SO₄, filtered and evaporated. The solid obtained was recrystallized from CH₃CN to give the title compound (170 mg) as white crystals.

m.p.: 254–256° C.

Analysis for C25H24F3N3O3S Calculated: C,59.63; H,4.80; N,8.34; Found C,59.58; H,5.10; N,8.57%.

EXAMPLE 84
4'-Trifluoromethyl-biphenyl-2-carboxylic Acid (4-[1-(3-cyano-benzyl)-piperidin-4-yl]-phenyl]-amide To a solution of 4'-trifluoromethyl-biphenyl-2-carboxylic acid (4-piperidin-4-yl]-phenyl)-amide trifluoroacetate salt. (0.23 g) in acetone (10 mL) containing K₂CO₃ (0.18 g) was added 3-cyano-benzyl bromide (0.086 g) and the mixture was heated at reflux. After 16 hours, the mixture was cooled at room temperature, the salts were removed by filtration, washed with acetone and the filtrate was evaporated under reduced presssure. The residue was purified by flash chromatography eluting with CH₂Cl₂/MeOH (98/2) and the oily residue was crystallized from diisopropyl ether to give the title compound (0.13 g) as white crystals.

m.p.: 124–126° C.

Analysis for C33H28F3N3O Calculated: C,73.45; H,5.23; N,7.79; Found: C,73.43; H,5.56; N,7.91%.

EXAMPLE 85

N-{4-[4-(3-Cyano-benzyl)-piperazin-1-yl]-phenyl}-2-pyrrol-1-yl-benzamide as a pale yellow solid (426 mg), m.p.: 174° C. from 2-pyrrol-1-yl-benzoic acid (538 mg) and 4-[4-(3-cyano-benzyl)-piperazin-1-yl]-phenylamine (700 mg).

Analysis for C29H27N5O Calculated C,75.46; H,5.90; N,15.17; Found: C,75.09; H,6.07; N,15.15%.

EXAMPLE 86

N-{4-[4-(3-Cyano-benzyl)-piperazin-1-yl]-phenyl}-2-pyridin-2-yl-benzamide as white crystals (200 mg), m.p.: 169–171° C. from 2-pyridin-2-yl-benzoic acid (199 mg) and 4-[4-(3-cyano-benzyl)-piperazin-1-yl]-phenylamine (292 mg).

Analysis for C30H27N5O Calculated: C,76.09; H,5.75; N,14.79; Found C,76.04; H,5.94; N,14.47%.

EXAMPLE 87

4'-Trifluoromethyl-biphenyl-2-carboxylic Acid [4-[4-(3-cyano-benzyl)-piperazin-1-yl]-phenyl]-amide Citrate Salt To a solution of 4'-trifluoromethyl-biphenyl-2-carboxylic acid [4-[4-(3-cyano-benzyl)-piperazin-1-yl]-phenyl]-amide (0.2 g) in MeOH (15 mL) was added citric acid (71 mg) and the resulting solution was stirred at room temperature. The solution was then evaporated to dryness and the solid was triturated in Et$_2$O, filtered and dried to give the title compound (0.15 g) as a white powder.

m.p.: 120° C.

EXAMPLE 88

4'-Trifluoromethl-biphenyl-2-carboxylic Acid [4-[4-(3-cyano-benzyl)-piperazin-1-yl]-phenyl]-amide hydrochloride Salt To a solution of 4'-trifluoromehtyl-biphenyl-2-carboxylic acid [4-[4-(3-cyano-benzyl)-piperazin-1-yl]-phenyl]-amide (0.2 g) in AcOEt (25 mL) was added 1N hydrochloric acid (0.9 mL) and the resulting solution was stirred at room temperature for 1.5 hours. The solution was then evaporated to dryness and the solid was recrystallized from AcOEt/hexane to give the title compound (0.18 g) as a white power.

m.p.: 165° C.

Biological Assay

Primary human hepatocytes were seeded at 50 000 cells/well in 96 well plates. After an overnight adhesion phase, cells were incubated with compounds for 8 hours in RPMI medium containing 1% FCS, 4 μg/ml insulin, 100 nM dexamethasone and 50 μCi/ml $^{35}$S-methionine. Compounds were dissolved in DMSO and tested onto cells from 1 μM to 1.6 nM. Production of radiolabeled apoB-100 and apoA-1 (used as a selectivity control) was quantified by analysis of supernatants using SDS AGE and exposure of gels onto Phosphorimager screens. Inhibition of apo-100 and apoA-1 secretion by compounds was calculated taking untreated cells as controls, and IC$_{50}$ of each compound was determined on both apoproteins. The following results were obtained for a selection to compounds of the invention:

| Example no. | Primary human hepatocytes IC$_{50}$ (nM) |
|---|---|
| 1 | 13 |
| 3 | 18 |
| 63 | 20 |
| 4 | 12 |
| 3 | 13 |
| 62 | 10 |
| 2 | 18 |
| 6 | 18 |
| 64 | 19 |
| 5 | 15 |

Tablet Compositions

The following compositions A and B can be prepared by wet granulation of ingredients (a) to (c) and (a) to (d) with a solution of povidone, followed by addition of the magnesium stearate and compression.

Composition A

| | | mg/tablet | mg/tablet |
|---|---|---|---|
| (a) | Active ingredient | 250 | 250 |
| (b) | Lactose B.P. | 210 | 26 |
| (c) | Sodium Starch Glycollate | 20 | 12 |
| (d) | Povidone B.P. | 15 | 9 |
| (e) | Magnesium Stearate | 5 | 3 |
| | | 500 | 300 |

Composition B

| | | mg/tablet | mg/tablet |
|---|---|---|---|
| (a) | Active ingredient | 250 | 250 |
| (b) | Lactose 150 | 150 | — |
| (c) | Avicel PH 101 | 60 | 26 |
| (d) | Sodium Starch Glycollate | 20 | 12 |
| (e) | Povidone B.P. | 15 | 9 |
| (f) | Magnesium Stearate | 5 | 3 |
| | | 500 | 300 |

Composition C

| | mg/tablet |
|---|---|
| Active ingredient | 100 |
| Lactose | 200 |
| Starch | 50 |
| Povidone | 5 |
| Magnesium Stearate | 4 |
| | 359 |

The following compositions D and E can be prepared by direct compression of the admixed ingredients. The lactose used in composition E is of the direct compression type.

Composition D

| | mg/tablet |
|---|---|
| Active ingredient | 250 |
| Magnesium Stearate | 4 |
| Pregelatinised Starch NF15 | 146 |
| | 400 |

Composition E

| | mg/tablet |
|---|---|
| Active ingredient | 250 |
| Magnesium Stearate | 5 |
| Lactose | 145 |
| Avicel | 100 |
| | 500 |

Composition F (Controlled release composition)

| | | mg/tablet |
|---|---|---|
| (a) | Active ingredient | 500 |
| (b) | Hydroxypropylmethylcellulose (Methocel K4M Premium) | 112 |
| (c) | Lactose B.P. | 53 |
| (d) | Povidone B.P.C. | 28 |
| (e) | Magnesium Stearate | 7 |
| | | 700 |

The composition can be prepared by wet granulation of ingredients (a) to (c) with a solution of povidone, followed by addition of the magnesium stearate and compression.

Composition G (Enteric-coated tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-coated controlled release tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule Compositions
Composition A

Capsules can be prepared by admixing the ingredients of Composition D above and filling two-part hard gelatin capsules with the resulting mixture. Composition B (infra) may be prepared in a similar manner.

Composition B

| | | mg/capsule |
|---|---|---|
| (a) | Active ingredient | 250 |
| (b) | Lactose B.P. | 143 |
| (c) | Sodium Starch Glycollate | 25 |
| (d) | Magnesium Stearate | 2 |
| | | 420 |

Composition C

| | | mg/capsule |
|---|---|---|
| (a) | Active ingredient | 250 |
| (b) | Macrogol 4000 BP | 350 |
| | | 600 |

Capsules can be prepared by melting the Macrogol 4000 BP, dispersing the active ingredient in the melt and filling two-part hard gelatin capsules therewith.

Composition D

| | mg/capsule |
|---|---|
| Active ingredient | 250 |
| Lecithin | 100 |
| Arachis Oil | 100 |
| | 450 |

Capsules can be prepared by dispersing the active ingredient in the lecithin and arachis oil and filling soft, elastic gelatin capsules with the dispersion.

Composition E (Controlled release capsule)

| | | mg/capsule |
|---|---|---|
| (a) | Active ingredient | 250 |
| (b) | Microcrystalline Cellulose | 125 |
| (c) | Lactose BP | 125 |
| (d) | Ethyl Cellulose | 13 |
| | | 513 |

The controlled release capsule composition can be prepared by extruding mixed ingredients (a) to (c) using an extruder, then spheronising and drying the extrudate. The dried pellets are coated with a release controlling membrane (d) and filled into two-part, hard gelatin capsules.

| Composition F (Enteric capsule) | | |
|---|---|---|
| | | mg/capsule |
| (a) | Active ingredient | 250 |
| (b) | Microcrystalline Cellulose | 125 |
| (c) | Lactose BP | 125 |
| (d) | Cellulose Acetate Phthalate | 50 |
| (e) | Diethyl Phthalate | 5 |
| | | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-coated controlled release capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

| (iii) Intravenous injection composition | |
|---|---|
| Active ingredient | 0.200 g |
| Sterile, pyrogen-free phosphate buffer (pH 9.0) to | 10 ml |

The active ingredient is dissolved in most of the phosphate buffer at 35–40° C., then made up to volume and filtered through a sterile micropore filter into sterile 10 ml glass vials (Type 1) which are sealed with sterile closures and overseals.

| (iv) Intramuscular injection composition | |
|---|---|
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

| (v) Syrup composition | |
|---|---|
| Active ingredient | 0.25 g |
| Sorbitol Solution | 1.50 g |
| Glycerol | 1.00 g |
| Sodium Benzoate | 0.005 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

| (vi) Suppository composition | |
|---|---|
| | mg/suppository |
| Active ingredient | 250 |
| Hard Fat, BP (Witepsol H15 - Dynamit NoBel) | 1770 |
| | 2020 |

One-fifth of the Witepsol H15 is melted in a stearh-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38–40° C., 2.02 g aliquots of the mixture are filled into suitable plastic moulds and the suppositories allowed to cool to room temperature.

| (vii) Pessary composition | |
|---|---|
| | mg/pessary |
| Active ingredient (631 m) | 250 |
| Anhydrous Dextrose | 380 |
| Potato Starch | 363 |
| Magnesium Stearate | 7 |
| | 1000 |

The above ingredients are mixed directly and pessaries prepared by compression of the resulting mixture.

| (viii) Transdermal composition | |
|---|---|
| Active ingredient | 200 mg |
| Alcohol USP | 0.1 ml |
| Hydroxyethyl cellulose | |

The active ingredient and alcohol USP are gelled with hydroxyethyl cellulose and packed in a transdermal device with a surface area of 10 cm$^2$.

What is claimed is:

1. A compound of formula (Ie)

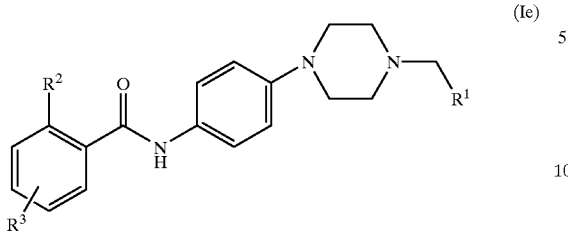

wherein
R¹ is selected from the following groups
(i) aminocarbonyl,
(ii) phenyl, optionally substituted by $C_{1-6}$ alkyl, cyano, halogen, $C_{1-6}$alkoxy, $C_{1-3}$perfluoroalkyl, hydroxycarbonyl, $C_{1-4}$alkoxycarbonyl, aminocarbonyl, methylenedioxy, nitro, $C_{1-6}$ acyl, phenyl, or an optionally substituted oxadiazolyl, where optional substitution is effected by $C_{1-4}$ alkyl or $C_{1-3}$perfluoroalkyl, or
(iii) an optionally substituted aromatic heterocyclyl having monocyclic radicals and fused polycyclic radicals, wherein said radicals contain a total of from 5–10 ring atoms and are selected from the group consisting of indolyl, pyrrolyl, thienyl, furanyl, imidazolyl, pyrazolyl, thiazolyl, pyridyl, and pyrazinyl, where optional substitution is effected by $C_{1-4}$ alkyl;
R² represents phenyl, optionally substituted by one or two groups independently selected from halogen, $C_{1-3}$perfluoroalkyl, $C_{1-4}$alkyl and $C_{1-4}$alkoxy groups;
R³ represents hydrogen, halogen, $C_{1-4}$alkyl or $C_{1-4}$alkoxy;
or a physiologically acceptable salt thereof.

2. A compound according to claim 1 selected from the group consisting of:
4'-Trifluoromethyl-biphenyl-2-carboxylic acid [4-[4-(cyano-benzyl)-piperazin-1-yl]-phenyl]-amide;
4'-Isopropyl-5-methyl-biphenyl-2-carboxylic acid [4-[4-(3-cyano-benzyl)-piperazin-1-yl]-phenyl]-amide;
4'-Isopropyl-6-methoxy-biphenyl-2-carboxylic acid [4-[4-(3-cyano-benzyl)-piperazin-1-yl]-phenyl]-amide;
4'-Isopropyl-4-methyl-biphenyl-2-carboxylic acid [4-[4-(3-cyano-benzyl)-piperazin-1-yl]-phenyl]-amide;
6-Methyl-4'-trifluoromethyl-biphenyl-2-carboxylic acid [4-[4-(3-cyano-benzyl)-piperazin-1-yl]-phenyl]-amide;
4'-isopropyl-5-methyl-biphenyl-2-carboxylic acid (4-[3-(3-methyl-[1,2,4]oxadiazol-5-yl)-benzyl]-piperazin-1-yl}-phenyl)-amide;
5-Chloro-4'-isopropyl-biphenyl-2-carboxylic acid [4-[4-(3-cyano-benzyl)-piperazin-1-yl]-phenyl]-amide;
6-Methoxy-4'-trifluoromethyl-biphenyl-2-carboxylic acid [4-[4-(3-cyano-benzyl)-piperazin-1-yl]-phenyl]-amide;
5-Methyl-4'-trifluoromethyl-biphenyl-2-carboxylic acid [4-[4-(3-cyano-benzyl)-piperazin-1-yl]-phenyl]-amide;
5-Chloro-4'-trifluoromethyl-biphenyl-2-carboxylic acid [4-[4-(3-cyano-benzyl)-piperazin-1-yl]-phenyl]-amide;
Biphenyl-2-carboxylic acid [4-[4-(3-cyano-benzyl)-piperazin-1-yl]-phenyl]-amide;
5-Methoxy-biphenyl-2-carboxylic acid [4-[4-(3-cyano-benzyl)-piperazin-1-yl]-phenyl]-amide;
4-Chloro-4'-trifluoromethyl-biphenyl-2-carboxylic acid [4-[4-(3-cyano-benzyl)-piperazin-1-yl]-phenyl]-amide;
4'-Isopropyl-biphenyl-2-carboxylic acid [4-[4(3-cyano-benzyl)-piperazin-1-yl]-phenyl]-amide;
5-Methoxy-4'-trifluoromethyl-biphenyl-2-carboxylic acid [4-[4-(3-cyano-benzyl)-piperazin-1yl]-phenyl]-amide;
4-Methyl -4'-trifluoromethyl-biphenyl-2-carboxylic acid [4-[4-(3-cyano-benzyl)-piperazin-1-yl]-phenyl]-amide;
4-Methoxy-4'-trifluoromethyl-biphenyl-2-carboxylic acid [4-[4-(3-cyano-benzyl)-piperazin-1-yl]-phenyl]-amide;
4'-Ethyl-biphenyl-2-carboxylic acid [4-[4-(3-cyano-benzyl)-piperazin-1-yl]-phenyl]-amide;
4'-Methoxy-biphenyl-2-carboxylic acid [4-[4-(3-cyano-benzyl)-piperazin-1-yl]-phenyl]-amide;
3'-Trifluoromethyl-biphenyl-2-carboxylic acid [4-[4-(3-cyano-benzyl)-piperazin-1-yl]-phenyl]-amide;
4'-Fluoro-biphenyl-2-carboxylic acid [4-[4-(3-cyano-benzyl)-piperazin-1-yl]-phenyl]-amide;
3',4'-Dimethyl-biphenyl-2-carboxylic acid [4-[4-(3-cyano-benzyl)-piperazin-1-yl]-phenyl]-amide;
2',4'-Dimethyl-biphanyl-2-carboxylic acid [4-[4-(3-cyano-benzyl)-piperazin-1-yl]-phenyl]-amide;
3',4'-Dimethoxy-biphenyl-2-carboxylic acid [4-[4-(3-cyano-benzyl)-piperazin-1-yl]-phenyl]-amide;
4'-Trifluoromethyl-biphenyl-2-carboxylic acid [3-[4-(3-cyano-benzyl)-piperazin-1-yl-3-phenyl]-amide;
4'-Tifluoromethyl-biphenyl-2-carboxylic acid [4-(4-carbamoylmethyl-piperazin-1-yl)-phenyl)-amide;
4'-Isopropyl-6-methoxy-biphenyl-2-carboxylic acid [4-(4-carbamoylmethyl-piperazin-1-yl)-phenyl]-amide
4'-Isopropyl-6-methyl-biphenyl-2-carboxylic acid [4-(4-carbamoylmethyl-piperazin-1-yl)-phenyl]-amide;
6-Methyl-4'-trifluoromethyl-biphenyl-2-carboxylic acid [4-(4-carbamoylmethyl-piperazin-1-yl)-phenyl]-amide;
4'-Trifluoromethyl-biphenyl-2-carboxylic acid [4-(4-(3-cyano-4-fluoro-benzyl)-piperazin-1-yl)-phenyl]-amide;
4'-Trifluoromethyl-biphenyl-2-carboxylic acid [4-(4-(3,4-methylenedioxy-benzyl)-piperazin-1-yl)-phenyl]-amide;
4'-Trifluoromethyl-biphenyl-2-carboxylic acid [4-(4-(3-nitro-benzyl)-piperazin-1-yl)-phenyl]-amide.;
4'-Trifluoromethyl-biphenyl-2-carboxylic acid {4-[4-(3-carbamoyl-benzyl)-piperazin-1-yl]-phenyl}-amide;
4'-Trifluoromethyl-biphenyl-2-carboxylic acid [4-[4-(3-methoxy-benzyl)-piperazin-1-yl]-phenyl]-amide;
4'-Trifluoromethyl-biphenyl-2carboxylic acid [4-[4-(4-fluoro-benzyl)-piperazin-1-yl]-phenyl]-amide;
4'-Trifluoromethyl-biphenyl-2-carboxylic acid [4-[4-(3-fluoro-benzyl)-piperazin-1-yl]-phenyl]-amide;
4'-Trifluoromethyl-biphenyl-2-carboxylic acid [4-(4-benzyl)-piperazin-1-yl]-phenyl]-amide;
4'-Trifluoromethyl-biphenyl-2-carboxylic acid [4-[4-(3-carbomethoxy-benzyl)-piperazin-1-yl]-phenyl]-amide;
4'-Trifluoromethyl-biphenyl-2-carboxylic acid [4-(4-pyridin-4-ylmethyl-piperazin-1-yl)-phenyl)-amide;
4'-Trifluoromethyl-biphenyl-2-carboxylic acid [4-(4-pyridin-2-ylmethyl-piperazin-1-yl)-phenyl)-amide;
4'-Trifluoromethyl-biphenyl-2-carboxylic acid [4-(4-pyrazin-2-ylmethyl-piperazin-1-yl)-phenyl)-amide;
4'-Trifluoromethyl-biphenyl-2-carboxylic acid [4-(4-thiazol-2-ylmethyl-piperazin-1-yl)-phenyl)-amide;
4'-Trifluoromethyl-biphenyl-2-carboxylic acid [4-[4-(1-methyl-1H-imidazol-2-ylmethyl)-piperazin-1-yl)-phenyl]-amide;

4'-Isopropyl-6methyl-biphenyl-2-carboxylic acid (4-(4-(3-(3-methyl-[1,2,4]oxadiazol-5-yl)-benzyl)-piperazine-1-yl)-phenyl)-amide;

4'-Trifluoromethyl-biphenyl-2-carboxylic acid [4-(4-(1H-pyrrol-2-ylmethyl)-piperazin-1-yl)-phenyl]-amide;

4'-Isopropyl-5-methyl-biphenyl-2-carboxylic acid [4-(4-(1H-pyrrol-2-ylmethyl)-piperazin-1-yl)-phenyl]-amide;

5-Methyl-4'-trifluoromethyl-biphenyl-2-carboxylic acid [4-(4-(1H-pyrrol-2-ylmethyl)-piperazin-1-yl)-phenyl]-amide;

4'-Trifluoromethyl-biphenyl-2-carboxylic acid [4-(4-(3-acetyl-benzyl)-piperazin-1-yl)-phenyl]-amide;

4'-Trifluoromethyl-biphenyl-2-carboxylic acid [4-(4-furan-2-ylmethyl-piperazin-1-yl)-phenyl]-amide;

4'-Isopropyl-6-methoxy-biphenyl-2-carboxylic acid [4-(4-(1H-pyrrol-2-ylmethyl)-piperazin-1-yl)-phenyl)-amide;

4'-Trifluoromethyl-biphenyl-2-carboxylic acid [4-(4-(1-methyl-1H-pyrrol-2-ylmethyl)-piperazin-1-yl)-phenyl]-amide;

4'-Trifluoromethyl-biphenyl-2-carboxylic acid [4-(4-thiophen-2-ylmethyl-piperazin-1-yl)-phenyl]-amide;

4'-Trifluoromethyl-biphenyl-2-carboxylic acid {4-[4-(1H-pyrazole-3-ylmethyl)-piperazine-1-yl]-phenyl}-amide;

4'-Trifluoromethyl-biphenyl-2-carboxylic acid [4-(4-thiophen-3-ylmethyl-piperazin-1-yl)-phenyl]-amide;

4'-Trifluoromethyl-biphenyl-2-carboxylic acid {4-[4-(5-fluoro-1H-indol-3-ylmethyl)-piperazin-1-yl]-phenyl}-amide;

4'-Isopropyl-6-methoxy'-biphenyl-2-carboxylic acid (4-(4-(3-(3-methyl-[1,2,4]oxadiazol-5-yl)-benzyl)-piperazine-1-yl)-phenyl)-amide;

4'-Trifluoromethyl-biphenyl-2-carboxylic acid (4-{4-[3-(5-trifluoromethyl-1,2,4]oxadiazol-3-yl)-benzyl]-piperazin-1-yl}-phenyl)-amide;

or a physiologically acceptable salt thereof.

3. A compound according to claim 2 selected from the group consistin of:

4'-Trifluoromethyl-biphenyl-2-carboxylic acid [4-[4-(3-cyano-benzyl)-piperazin-1-yl]-phenyl]-amide;

4'-Isopropyl-5-methyl-biphenyl-2-carboxylic acid [4-[4-(3-cyano-benzyl)-piperazin-1-yl]-phenyl]-amide;

4'-Isopropyl-6-methoxy-biphenyl-2-carboxylic acid [4-[4-(3-cyano-benzyl)-piperazin-1-yl]-phenyl]-amide 4'-Isopropyl-6-methyl-biphenyl-2-carboxylic acid [4-[4-(3-cyano-benzyl)-piperazin-1-yl]-phenyl]-amide;

6-Methyl-4'-trifluoromethyl-biphenyl-2-carboxylic acid [4-[4-(3-cyano-benzyl)-piperazin-1-yl]-phenyl]-amide;

4'-Isopropyl-5-methyl-biphenyl-2-carboxylic acid (4-{3-(3-methyl-[1,2,4]oxadiazol-5-yl)-benzyl]-piperazin-1-yl}-phenyl)-amide;

4'-Trifluoromethyl-biphenyl-2-carboxylic acid [4-(4-carbamoylmethyl-piperazin-1-yl)-phenyl]-amide;

4'-Isopropyl-6-methoxy-biphenyl-2-carboxylic acid [4-(4-carbamoylmethyl-piperazin-1-yl)-phenyl]-amide;

4'-Isopropyl-6-methyl-biphenyl-2-carboxylic acid [4-(4-carbamoylmethyl-piperazin-1-yl)-phenyl]-amide;

4'-Isopropyl-6-methyl-biphenyl-2-carboxylic acid (4-(4-(3-(3-methyl-[1,2,4]oxadiazol-5-yl)-benzyl)-piperazine-1-yl)-phenyl)-amide;

4'-Trifluoromethyl-biphenyl-2-carboxylic acid [4-(4-(1H-pyrrol-2-ylmethyl)-piperazin-1-yl)-phenyl]-amide;

4'-Isopropyl-5-methyl-biphenyl-2-carboxylic acid [4-(4-(1H-pyrrol-2-ylmethyl)-piperazin-1-yl)-phenyl]-amide;

5-Methyl-4'-trifluoromethyl-biphenyl-2-carboxylic acid [4-(4-(1H-pyrrol-2-ylmethyl)-piperazin-1-yl)-phenyl]-amide;

or a physiologically acceptable salt thereof.

4. A pharmaceutical composition comprising a compound according to claim 1 or a physiologically acceptable salt thereof together with one or more pharmaceutically acceptable carriers.

5. A process for the preparation of a compound according to claim 1 comprising:

reacting a compound of formula (II) with a compound of formula R¹—CH₂—L

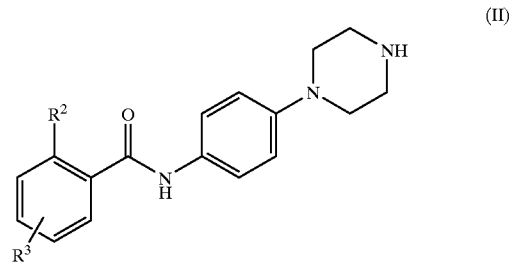

(II)

where L represents a halide leaving group.

6. A method for the treatment of atherosclerosis in a mammal, said method comprising administering an effective amount of a compound according to claim 1.

7. A method for the treatment of pancreatitis in a mammal, said method comprising administering an effective amount of a compound according to claim 1.

8. A method for the treatment of non-insulin dependent diabetes mellitus in a mammal, said method comprising administering an effective amount of a compound according to claim 1.

9. A method for the treatment of coronary heart disease in a mammal, said method comprising administering an effective amount of a compound according to claim 1.

10. A method for lowering serum lipid levels in a mammal in need thereof, said method comprising administering an effective amount of a compound according to claim 1.

11. A method for treating a condition associated with elevated serum lipid levels in a mammal, said method comprising administering an effective amount of a compound according to claim 1.

12. The method according to claim 11, wherein the condition associated with elevated serum lipid levels is selected from the group consisting of hyperlipemia, hyperlipidemia, hyperlipoproteinemia, hypercholesterolemia, and hypertriglyceridemia.

* * * * *